(12) United States Patent
Blaszczak et al.

(10) Patent No.: US 8,076,514 B2
(45) Date of Patent: Dec. 13, 2011

(54) PHENYL COMPOUNDS AND THEIR USE IN THE TREATMENT OF TYPE II DIABETES

(75) Inventors: Larry Chris Blaszczak, Indianapolis, IN (US); Shon Roland Pulley, Noblesville, IN (US); Michael Alan Robertson, Indianapolis, IN (US); Scott Martin Sheehan, Carmel, IN (US); Qing Shi, Carmel, IN (US); Brian Morgan Watson, Carmel, IN (US); Michael Robert Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 938 days.

(21) Appl. No.: 11/996,123

(22) PCT Filed: Jul. 14, 2006

(86) PCT No.: PCT/US2006/027673
§ 371 (c)(1),
(2), (4) Date: Jan. 18, 2008

(87) PCT Pub. No.: WO2007/015807
PCT Pub. Date: Feb. 8, 2007

(65) Prior Publication Data
US 2008/0221217 A1 Sep. 11, 2008

Related U.S. Application Data

(60) Provisional application No. 60/700,784, filed on Jul. 20, 2005.

(51) Int. Cl.
*C07C 233/65* (2006.01)
*A61K 31/165* (2006.01)
(52) U.S. Cl. ........................ 564/165; 514/620
(58) Field of Classification Search .................. 564/165; 514/620
See application file for complete search history.

(56) References Cited

U.S. PATENT DOCUMENTS

| 5,508,407 | A | 4/1996 | Kaldor |
| 5,554,653 | A | 9/1996 | Hui et al. |
| 5,714,142 | A | 2/1998 | Blaney et al. |
| 2004/0167133 | A1 | 8/2004 | Edmondson et al. |
| 2004/0236102 | A1 | 11/2004 | Brockunier et al. |

FOREIGN PATENT DOCUMENTS

| EP | 526009 A1 | 2/1993 |
| EP | 604184 A1 | 6/1994 |
| WO | WO 95/09843 A1 | 4/1995 |
| WO | WO 96/41795 A1 | 12/1996 |
| WO | WO 03/000181 A2 | 1/2003 |
| WO | WO 03/004498 A1 | 1/2003 |
| WO | WO 03/082817 A2 | 1/2003 |
| WO | WO 03/034989 A2 | 5/2003 |
| WO | WO 2004/037169 A2 | 5/2004 |
| WO | WO 2007/015767 | 2/2007 |
| WO | WO 2007/015805 | 2/2007 |

OTHER PUBLICATIONS

RN 177739-96-7(corresponding to US 5,508,407, 1996.*
Yuichi Kanoaka et al., "Application of the Robinson Dehydrogenation Reaction", Chemical and Pharmaceutical Bulletin, 1959(5), 589-594, XP008071731.
Xu J et al., "Discovery of potent and selective phenylalanine based dipeptidyl peptidase IV inhibitors", Bioorganic & Medicinal Chemistry Letters, 15(10), 2533-2536, ISNN: 0960-894X, XP004877719.
C. Rummey et al, "In silico fragment-based discovery of DPP-IV S1 pocket binders", Bioorganic & Medicinal Chemistry Letters 16 (2006) pp. 1405-1409.
J. Peters et al, "Aminomethylpyrimidines as novel DPP-IV inhibitors: A $10^5$-fold activity increase by optimization of aromatic substituents", Bioorganic & Medicinal Chemistry Letters 14 (2004), pp. 1491-1493.

* cited by examiner

*Primary Examiner* — Shailendra Kumar
(74) *Attorney, Agent, or Firm* — James B. Myers

(57) ABSTRACT

The present invention is directed to compounds of formula (I) or a pharmaceutically acceptable salt thereof; wherein A is (xx); X is selected from CH, CF and N, R5 is selected from H, $C_1$-$C_6$ alkyl, $C_1$-$C_6$ fluoroalkyl, and —OR12, R9 is selected from H and —C(O)NR1OR11, R12 is selected from H, $C_1$-$C_6$ alkyl and $C_3$-$C_6$ cycloalkyl for use as inhibitors of the DPP-IV enzyme in the treatment or prevention of conditions including Type II diabetes.

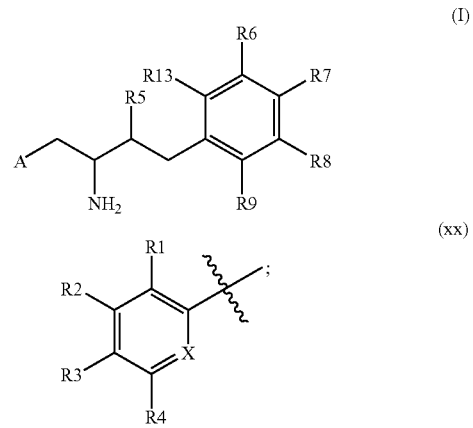

17 Claims, No Drawings

PHENYL COMPOUNDS AND THEIR USE IN THE TREATMENT OF TYPE II DIABETES

REFERENCE TO RELATED APPLICATION

This application is submitted as a U.S. national phase entry, pursuant to 35 U.S.C. §371, of PCT/US2006/027673, filed on 14 Jul. 2006, which claims the benefit of U.S. provisional patent application Ser. No. 60/700,784, filed 20 Jul. 2005, each of which is incorporated by reference herein.

BACKGROUND OF THE INVENTION

Diabetes is a chronic disease that features abnormal glucose homeostasis, the disease has been differentiated into two forms; Type I or insulin-dependent diabetes mellitus (IDDM) and Type II or non-insulin-dependent diabetes mellitus (NIDDM). Type II diabetes accounts for 90% of all cases of diabetes and in 1994 was estimated by the World Health Organization to affect 2-3% of the world's population with diagnosis rates rising at 4-5% per year.

The initial stage of Type II diabetes is characterized by insulin resistance which is initially compensated, in part, by increased production of insulin by pancreatic β cells, over time these cells become exhausted and insulin production decreases. The combined effects of insulin resistance and decreased insulin production reduce glucose uptake and utilization by skeletal muscle and prevent insulin-mediated suppression of hepatic glucose output. As the disease progresses blood glucose levels increase, postprandial hyperglycaemia is observed which upon further development leads to a state of fasting hyperglycaemia.

Type II diabetes is a component of a disease cluster known as metabolic syndrome, comprising a variety of disorders including glucose intolerance/insulin resistance, arterial hypertension, dyslipidaemia and obesity. For Type II diabetic patients suffering from poor glycaemic control the major cause for concern are chronic complications such as retinopathy, nephropathy, neuropathy and atherosclerosis.

The treatments currently available for Type II diabetes range from increased exercise in combination with decreased calorific intake to, when other treatment options fail, the injection of exogenous insulin. Within this range of treatments are a number of oral pharmacological agents which may be administered individually or, for patients where the disease is more advanced, in combination to achieve better glycaemic control.

Current oral pharmacological agents include sulfonylureas (e.g. tolbutamide) and glinides which stimulate the pancreatic β cells, increasing insulin secretion. Also, acarbose which is an α-glucosidase inhibitor that reduces the rate of intestinal carbohdrate digestion and therefore absorption. Biguanidines, such as metformin and glitazones, counter insulin resistance by decreasing hepatic glucose output and increasing muscle insulin sensitivity. The glitazones (thiazolidinediones) exert their action by acting as agonists of the peroxisome proliferator activated receptor (PPAR) and more particularly the PPAR-γ receptor.

As a consequence of side effects associated with the current oral pharmacological agents, namely, sulfonylurea and glinide induced hypoglycaemia, acarbose induced gastrointestinal disturbances, metformin induced lactic acidosis and glitazone induced liver toxicity, there continues to be a demand for the development of alternative oral antidiabetic agents.

There are a wide variety of alternative approaches to glycaemic control currently under investigation. Alternative approaches under investigation include, treatment with PPAR-α or PPAR-δ agonists, rexinoid X receptor (RXR) agonists, protein tyrosine phosphotase 1B (PTP-1B) inhibitors and glycogen synthase kinase (GSK)-3 inhibitors.

Dipeptidyl peptidase IV (DPP-IV) is a widely expressed glycoprotein present in cells in most tissues, including the kidney, gastrointestinal tract and liver and is responsible for the rapid degradation of several regulatory peptides including the incretin hormones, glucagon-like peptide-1 (GLP-1) and glucose-dependent insulinotropic polypeptide (GIP). GLP-1 is released from the intestinal tract wall into the bloodstream in response to nutrient ingestion and is an integral component in the physiological control of insulin release, and therefore the regulation of blood glucose. Inhibiting DPP-IV enhances the body's normal homeostatic mechanisms resulting in increased levels of GLP-1, lead to higher plasma insulin concentrations and thus regulate blood glucose.

Advantageously, DPP-IV inhibitors in utilising the body's normal homeostatic mechanisms, insulin levels will only be increased at appropriate times such as in response to nutrient ingestion. This mode of action significantly reduces the risk of hypoglycaemia, and highlights DPP-IV inhibitors as a target of interest for the development of alternative oral antidiabetic agents.

Compounds that are inhibitors of DPP-IV and which may be useful in the treatment of diabetes have been described in the art. These compounds include thiazolidine derivatives (e.g. *Drugs of the Future*, (2001) 26: 859-864, WO 99/61431, U.S. Pat. No. 6,110,949, WO 03/037327) and pyrrolidine derivatives (e.g. *Diabetes*, (2002) 51: 1461-1469, WO 98/19998, WO 01/40180, WO 03/037327). Other compounds include piperidine, piperizine and morpholine derivatives (e.g. WO 03/000181, WO 03/082817). Still others include pyridine derivatives (e.g. WO 03/068748, WO 03/068757, WO 05/042488)

The present invention relates to phenyl compounds which are inhibitors of the DPP-IV enzyme, pharmaceutical compositions containing them as active ingredient, methods for the treatment or prevention of diseases in which the DPP-IV enzyme is involved, to their use as medicaments and to their use in the manufacture of medicaments for the treatment or prevention of diseases in which the DPP-IV enzyme is involved, such as diabetes and particularly Type II diabetes.

The compounds of the present invention are described by structural formula I:

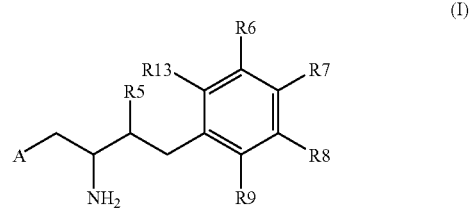

(I)

wherein
A is

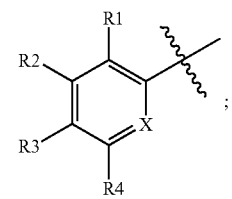

R1 is selected from H, halo, $C_1$-$C_4$ alkyl, $C_1$-$C_4$ alkoxy, $C_1$-$C_4$ haloalkyl, $C_1$-$C_4$ haloalkoxy, CN and hydroxy;

R2, R3, and R4 are independently selected from H, halo, methyl, ethyl, methoxy, $C_1$-$C_2$ haloalkyl, $C_1$ haloalkoxy, CN and hydroxy;

X is selected from CH, CF and N;

R5 is selected from H, $C_1$-$C_6$ alkyl, $C_1$-$C_6$ fluoroalkyl, and —OR12;

R6 is selected from H, halo, $C_1$-$C_6$ alkyl, $C_1$-$C_6$ alkoxy, $C_1$-$C_4$ alkyl-O— $C_1$-$C_4$ alkyl, $C_1$-$C_6$ haloalkyl, hydroxy $C_1$-$C_6$ alkyl, CN and hydroxy, or R6 and R7 combine to form a 5-8 membered carbocyclic ring or a 5-6 membered heteroaryl ring optionally substituted with 1-3 substituents selected from methoxy, Cl, F, $CH_3$ and $CF_3$;

R7 and R8 are independently selected from H, halo, $C_1$-$C_6$ alkyl, aryl, heteroaryl, $C_1$-$C_6$ alkylaryl, $C_1$-$C_6$ alkylheteroaryl, $C_1$-$C_6$ alkoxy, $C_1$-$C_6$ alkyl-O—$C_1$-$C_6$ alkyl, $C_1$-$C_6$ haloalkyl, hydroxy $C_1$-$C_6$ alkyl, CN and hydroxy or R7 and R8 combine to form a 5-8 membered carbocyclic ring or a 5-6 membered heteroaryl ring optionally substituted with 1-3 substituents selected from methoxy, Cl, F, $CH_3$ and $CF_3$;

R9 is selected from H and —C(O)NR10R11;

R10 and R11 are independently selected from H, $C_1$-$C_6$ alkyl, $C_1$-$C_6$ haloalkyl, aryl, heteroaryl, $C_1$-$C_6$ alkylaryl and $C_1$-$C_6$ alkylheteroaryl or R10 and R11 combine with the N of R9 to form a 4 to 8 membered heterocyle;

where R7, R8, R10 or R11 are aryl, heteroaryl, $C_1$-$C_6$ alkylaryl or $C_1$-$C_6$ alkylheteroaryl the aryl or heteroaryl substituents are optionally substituted with 1-3 substituents selected from methoxy, Cl, F, $CH_3$ and $CF_3$;

R12 is selected from H, $C_1$-$C_6$ alkyl and $C_3$-$C_6$ cycloalkyl;

R13 is selected from H, halo, methyl, ethyl, methoxy, $C_1$-$C_2$ haloalkyl, $C_1$ haloalkoxy, CN and hydroxy; with the proviso that where R1, R2, R3 and R4 are H and X is CH at least one of R6, R7, R8, R9 or R13 is not H; and with the proviso that where R6, R7, R8, R9 and R13 are H at least one of R1, R2, R3 or R4 is not H or X is not CH; and with the further proviso that when R1, R2, R3, R4, R6, R7, R8, R9 and R13 are H and X is CH that R5 is not H; or a pharmaceutically acceptable salt thereof.

A preferred species of the compounds of formula I are compounds of formula II:

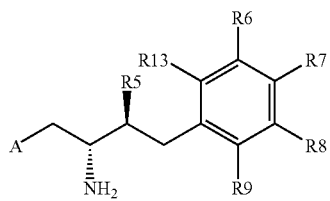

(II)

or a pharmaceutically acceptable salt thereof wherein A, R5, R6, R7, R8, R9 and R13 are as defined herein.

A preferred species of the compounds of formula I are compounds of formula Ia:

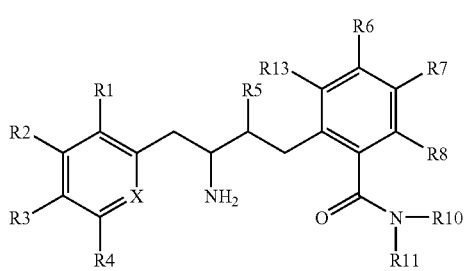

(Ia)

or a pharmaceutically acceptable salt thereof wherein R1, R2, R3, R4, R5, R6, R7, R8, R10, R11 and R13 are as defined herein.

A preferred species of the compounds of formula I are compounds of formula IIa:

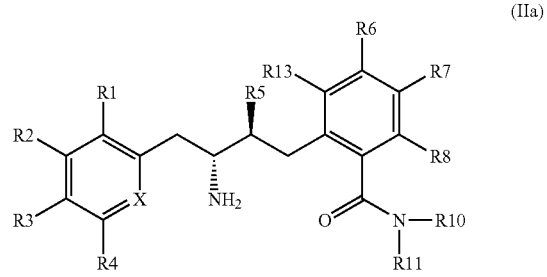

(IIa)

or a pharmaceutically acceptable salt thereof wherein R1, R2, R3, R4, R5, R6, R7, R8, R10, R11 and R13 are as defined herein.

A preferred species of the compounds of formula I are compounds of formula Ib:

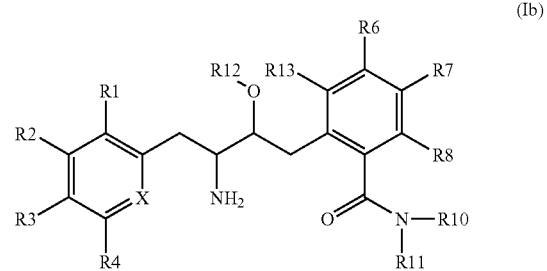

(Ib)

or a pharmaceutically acceptable salt thereof wherein R1, R2, R3, R4, R6, R7, R8, R10, R11, R12 and R13 are as defined herein.

A preferred species of the compounds of formula I are compounds of formula IIb:

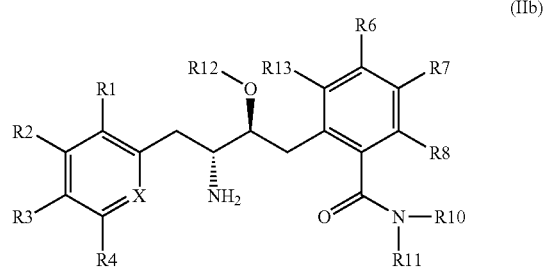

(IIb)

or a pharmaceutically acceptable salt thereof wherein R1, R2, R3, R4, R6, R7, R8, R10, R11, R12 and R13 are as defined herein.

A preferred species of the compounds of formula I are compounds of formula Ic:

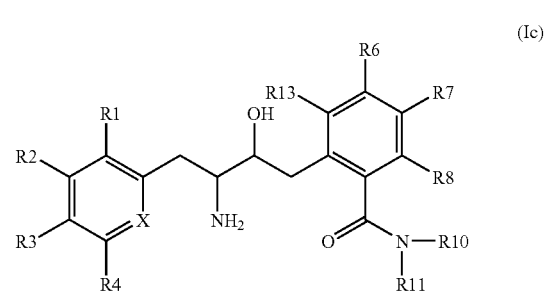

(Ic)

or a pharmaceutically acceptable salt thereof wherein R1, R2, R3, R4, R6, R7, R8, R10, R11 and R13 are as defined herein.

A preferred species of the compounds of formula I are compounds of formula IIc:

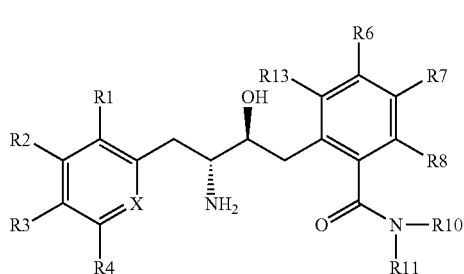

or a pharmaceutically acceptable salt thereof wherein R1, R2, R3, R4, R6, R7, R8, R10, R11 and R13 are as defined herein.

In the present invention it is preferred that R1 and R4 are independently selected from H, F, Cl, CH₃ and CF₃, it is more preferred that R1 and R4 are independently selected from F, Cl and CH₃, more preferably R1 and R4 are independently selected from F and Cl, most preferably R1 is F and R4 is either Cl or F.

In the present invention it is preferred that R5 is —OR12 wherein R12 is as defined herein.

In the present invention it is preferred that where X is N, R1 is selected from H, F and CH₃.

In the present invention it is preferred that where X is CH, at least one of R1, R2, R3 or R4 is not H.

In the present invention it is preferred that where R9 is H, R5 is not H.

In the present invention it is preferred that R2 and R3 are independently selected from H, F, Cl, CH₃ and CF₃, it is more preferred that R2 and R3 are independently selected from H, F and Cl, more preferably R2 and R3 are independently selected from H and F, most preferably R2 is H and R3 is F.

In the present invention it is preferred that R6, R7 and R8 are independently selected from H, F, Cl, CH₃ and OCH₃, more preferably R6 is H or Cl, most preferably R7 and R8 are H, most preferably R6 is Cl.

In the present invention it is preferred that R7 combines with R6 or R8 to form a 5-6 membered heteroaryl ring selected from pyridyl, pyrimidyl, pyrrolyl, pyrazolyl, isoxazolyl, isothiazolyl, imidazolyl, oxazolyl or thiazolyl, optionally substituted with 1-3 substituents selected from methoxy, Cl, F, CH₃ and CF₃; preferably R7 combines with R6 or R8 to form a pyrrolyl, pyrazolyl, isoxazolyl, isothiazolyl, imidazolyl, oxazolyl or thiazolyl substituent optionally substituted with 1-2 substituents selected from methoxy, Cl, F, CH₃ and CF₃; more preferably R7 combines with R6 or R8 to form a pyrazolyl, isoxazolyl, imidazolyl or oxazolyl substituent optionally substituted with 1 substituent selected from methoxy, Cl, F, CH₃ and CF₃; preferably R7 combines with R6 or R8 to form a isoxazolyl or oxazolyl substituent optionally substituted with 1 substituent selected from methoxy, Cl, F, CH₃ and CF₃.

In the present invention it is preferred that R9 is C(O)NR10R11 where R10 and R11 are as defined herein.

In the present invention it is preferred that R10 and R11 are independently selected from H, $C_1$-$C_4$ alkyl, aryl and $C_1$-$C_4$ alkylaryl wherein the aryl substituent of $C_1$-$C_6$ alkylaryl is optionally substituted with 1-3 substituents selected from methoxy, Cl, F, CH₃ and CF₃, more preferably R10 and R11 are independently selected from H, methyl, isopropyl, t-butyl, phenyl, benzyl, 1-methyl benzyl and 1,1-dimethyl benzyl wherein phenyl and benzyl substituents are optionally substituted with 1-3 substituents selected from methoxy, Cl, F, CH₃ and CF₃, most preferably R10 is H and R11 is t-butyl.

In the present invention it is preferred that X is selected from CH and CF, most preferably X is CH.

In the present invention it is preferred that R12 is selected from CH₃ and H, most preferably R12 is H.

In the present invention it is preferred that R13 is selected from H, F, Cl, CH₃ and CF₃, it is more preferred that R13 is selected from H, F and CH₃, most preferably R13 is H.

The compounds of formula I have been found to act as inhibitors of the DPP-IV enzyme in vitro. More particularly the compounds of formula I show selectivity for inhibition of the DPP-IV enzyme over the DPP 8 and/or DPP 9 enzyme.

The present invention provides pharmaceutical compositions comprising a compound of fomula I, or a pharmaceutically acceptable salt thereof together with a pharmaceutically acceptable diluent or carrier.

The present invention provides a method for the treatment or prevention of a disorder associated with DPP-IV dysfunction in mammals, which comprises administering a compound of formula I, or a pharmaceutically acceptable salt thereof, to a human being or animal in need thereof.

The present invention also provides a method for the treatment or prevention of a condition selected from type II diabetes, obesity, hyperglycemia and a lipid disorder, which comprises administering a compound of formula I, or a pharmaceutically acceptable salt thereof, to a human being or animal in need thereof.

The present invention further provides a method for the treatment or prevention of a lipid disorder, which comprises administering a compound of formula I, or a pharmaceutically acceptable salt thereof, to a human being or animal in need thereof wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use as a pharmaceutical; and a compound of formula I, or a pharmaceutically acceptable salt thereof for use in the treatment or prevention of type II diabetes, obesity, hyperglycemia or a lipid disorder.

The present invention also provides a compound of formula I, or a pharmaceutically acceptable salt thereof for use in the treatment or prevention of a lipid disorder, wherein said lipid disorder is selected from dyslipidemia, hyperlipidemia, hypertriglyceridemia, hypercholesterolemia, low HDL and high LDL.

Further, the present invention provides a compound of formula I, or a pharmaceutically acceptable salt thereof for use in the manufacture of a medicament for the treatment or prevention of type II diabetes, obesity, hyperglycemia or a lipid disorder.

The present invention provides a compound of formula I, or a pharmaceutically acceptable salt thereof for use in the manufacture of a medicament for the treatment or prevention of a lipid disorder, wherein said lipid disorder is selected from dyslipidemia, hyperlipidemia, hypertriglyceridemia, hypercholesterolemia, low HDL and high LDL.

As used throughout this specification, it is to be understood that where a group is qualified by "defined herein" or "herein defined" that said group encompasses the first occurring and broadest definition as well as each and all of the particular definitions for that group.

As used herein, the term "halo", unless otherwise stated, designate all four halogens, i.e. F, Cl, Br and I. Preferred halogens are F or Cl, most preferred is F.

As used herein the term "alkyl" includes both straight and branched chain alkyl groups and refers to $C_1$-$C_6$ alkyl chains, preferably $C_1$-$C_4$ alkyl chains.

As used herein, the term "$C_1$-$C_4$ alkyl" includes both straight chain and branched chain alkyl groups, such as methyl, ethyl, propyl, isopropyl, butyl, iso-butyl and t-butyl. Preferred $C_1$-$C_4$ alkyl groups include methyl, ethyl, propyl and isopropyl.

As used herein the term "$C_1$-$C_6$ alkyl" includes both straight chain and branched chain alkyl groups, such as methyl, ethyl, propyl, isopropyl, butyl, iso-butyl, t-butyl, pentyl, iso-pentyl, 1,2-dimethylpropyl and hexyl. Preferred $C_1$-$C_6$ alkyl groups include methyl, ethyl, propyl, isopropyl, butyl, iso-butyl and t-butyl As used herein the term "alkoxy" refers to an alkyl group as defined herein linked to an oxygen atom.

As used herein the term "$C_1$-$C_4$ alkoxy" includes methoxy, ethoxy, propoxy, isopropoxy, butoxy, iso-butoxy, t-butoxy. Preferred $C_1$-$C_4$ alkoxy groups include methoxy, ethoxy and isopropoxy.

As used herein the term "$C_1$-$C_6$ alkoxy" includes methoxy, ethoxy, propoxy, isopropoxy, tert-butoxy, pentoxy, iso-pentoxy and 1,2-dimethylpropoxy. Preferred $C_1$-$C_6$ alkoxy groups include methoxy, ethoxy, isopropoxy and tert-butoxy.

As used herein, the term "haloalkyl" refers to an alkyl group as defined herein wherein one or more of the hydrogens is replaced by a halo substituent as defined herein, which replacement can be at any site on the alkyl chain.

As used herein, the term "$C_1$-$C_2$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1, 1-trifluoromethyl and 1,1,1-trifluoroethyl.

As used herein, the term "$C_1$-$C_4$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1, 1-trifluoroethyl, 1,1,1-trifluoropropyl and 1,1,1,3,3,3-hexafluoroisopropyl. Preferred $C_1$-$C_4$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "$C_1$-$C_6$ haloalkyl" includes fluoromethyl, chloromethyl, difluoromethyl, dichloromethyl, trifluoromethyl, fluoroethyl, chloroethyl, 1,2-difluoroethyl, 1,1-difluoroethyl, 1,2-dichloroethyl, 1,1-dichloroethyl, 1,1, 1-trifluoroethyl, 1,1,1-trifluoropropyl and 1,1,1,3,3,3-hexafluoroisopropyl. Preferred $C_1$-$C_6$ haloalkyl groups include fluoromethyl, difluoromethyl, trifluoromethyl, fluoroethyl, 1,2-difluoroethyl, 1,1-difluoroethyl trifluoromethyl 1,2-difluoroethyl, 1,1-difluoroethyl, and 1,1,1-trifluoroethyl, most preferred are fluoromethyl, difluoromethyl and trifluoromethyl.

As used herein, the term "fluoroalkyl" refers to a haloalkyl group as defined herein where the halo substituent is fluorine.

As used herein, the term "$C_1$-$C_6$ fluoroalkyl" includes fluoromethyl, difluoromethyl, trifluoromethyl, fluoroethyl, 1,2-difluoroethyl, 1,1-difluoroethyl, trifluoromethyl, 1,1,1-trifluoroethyl, 1,1,1-trifluoropropyl and 1,1,1,3,3,3-hexafluoroisopropyl. Preferred $C_1$-$C_6$ fluoroalkyl groups include fluoromethyl, difluoromethyl, trifluoromethyl, 1,2-difluoroethyl, 1,1-difluoroethyl and 1,1,1-trifluoroethyl, most preferred are fluoromethyl, difluoromethyl and trifluoromethyl.

As used herein, the term "haloalkoxy" refers to an alkoxy group as defined herein wherein one or more of the hydrogens is replaced by a halo substituent as defined herein, which replacement can be at any site on the alkyl chain.

As used herein, the term "$C_1$ haloalkoxy" includes fluoromethoxy, chloromethoxyl, difluoromethoxy, dichloromethoxy, trifluoromethoxy. Preferred $C_1$ haloalkoxy groups include fluoromethoxy, difluoromethoxy and trifluoromethoxy.

As used herein, the term "$C_1$-$C_4$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_4$ haloalkoxy groups include fluoromethoxy, difluoromethoxy, trifluoromethoxy, 1,2-difluoroethoxy, 1,1-difluoroethoxy and 1,1,1,-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein, the term "$C_1$-$C_6$ haloalkoxy" includes fluoromethoxy, chloromethoxy, difluoromethoxy, dichloromethoxy, trifluoromethoxy, 1,2-difluoroethoxy, 1,1-difluoroethoxy, 1,2-dichloroethoxy, 1,1-dichloroethoxy, 1,1,1-trifluoroethoxy, 1,1,1-trifluoropropoxy and 1,1,1,3,3,3-hexafluoroisopropoxy. Preferred $C_1$-$C_6$ haloalkoxy groups include fluoromethoxy, difluoromethoxy, trifluoromethoxy, 1,2-difluoroethoxy, 1,1-difluoroethoxy and 1,1,1-trifluoroethoxy, most preferred are fluoromethoxy, difluoromethoxy, trifluoromethoxy, 1,2-difluoroethoxy, 1,1-difluoroethoxy and 1,1,1-trifluoroethoxy.

As used herein the term "hydroxy $C_1$-$C_6$ alkyl" refers to a $C_1$-$C_6$ alkyl group as defined herein wherein one of the hydrogens is replaced by an OH substituent, which replacement can be at any site on the alkyl chain, and includes hydroxy methyl, 1-hydroxy ethyl, 2-hydroxy ethyl, 2-hydroxy propyl, 3-hydroxy propyl, 2-hydroxy isopropyl, 3-hydroxy butyl and 4-hydroxy butyl. Preferred hydroxy($C_1$-$C_6$)alkyl groups include methanol, ethanol, isopropanol, and n-propanol.

As used herein the term "$C_1$-$C_4$ alkyl-O— $C_1$-$C_4$ alkyl" refers to a $C_1$-$C_4$ alkyl group as defined herein wherein one of the hydrogens is replaced by an oxygen substituent which replacement can be at any site on the alkyl chain, wherein the oxygen substituent is attached to a further $C_1$-$C_4$ alkyl group as defined herein, and includes methoxymethyl, ethoxymethyl, propoxymethyl, isopropoxymethyl, tert-butoxymethyl, methoxyethyl, ethoxyethyl, propoxyethyl, isopropoxyethyl and tert-butoxyethyl. Preferred $C_1$-$C_4$ alkyl-O— $C_1$-$C_4$ alkyl groups include methoxymethyl, ethoxymethyl, methoxyethyl and ethoxyethyl.

As used herein the term "$C_1$-$C_6$ alkyl-O— $C_1$-$C_6$ alkyl" refers to a $C_1$-$C_6$ alkyl group as defined herein wherein one of the hydrogens is replaced by an oxygen substituent which replacement can be at any site on the alkyl chain, wherein the oxygen substituent is attached to a further $C_1$-$C_6$ alkyl group as defined herein, and includes methoxymethyl, ethoxymethyl, propoxymethyl, isopropoxymethyl, tert-butoxymethyl, pentoxymethyl, methoxyethyl, ethoxyethyl, propoxyethyl, isopropoxyethyl, tert-butoxyethyl and pentoxyethyl. Preferred $C_1$-$C_6$ alkyl-O— $C_1$-$C_6$ alkyl groups include methoxymethyl, ethoxymethyl, methoxyethyl and ethoxyethyl.

As used herein, the term "$C_3$-$C_6$ cycloalkyl" means a monovalent unsubstituted saturated cyclic hydrocarbon radical having from 3 to 6 carbon atoms and includes cyclopropyl, cyclobutyl, cyclohexyl and cyclopentyl. Preferred $C_3$-$C_6$ cycloalkyl are cyclopropyl and cyclohexyl.

As used herein, the term "aryl" refers to a mono- or polycyclic aromatic ring system and includes phenyl, 1-naphthyl and 2-naphthal. Preferred aryl group is phenyl.

As used herein, the term "$C_1$-$C_4$ alkylaryl" refers to a $C_1$-$C_4$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_4$ alkylaryl include benzyl, 1-methyl benzyl and 1,1-dimethyl benzyl.

As used herein, the term "$C_1$-$C_6$ alkylaryl" refers to a $C_1$-$C_6$ alkyl group as defined herein wherein one of the hydrogens is replaced by an aryl substituent as defined herein which replacement can be at any site on the alkyl chain, and includes benzyl, phenylethyl, phenylpropyl, 1-methyl benzyl, phenyl butyl, 1,1-dimethyl benzyl, naphthylmethyl, naphthylethyl, naphthylpropyl, naphthylisopropyl, naphthylbutyl, naphthyl-t-butyl. Preferred $C_1$-$C_6$ alkylaryl include benzyl, 1-methyl benzyl and 1,1-dimethyl benzyl.

As used herein the term "carbocyclic ring" refers to a hydrocarbon ring fused to the phenyl substituent to which R6, R7 and R8 are attached, having from 5 to 8 carbon atoms and preferably 5 or 6 carbon atoms.

As used herein the term "heteroaryl" includes both monocyclic and bicyclic aromatic groups and includes 5-6-membered heteroaryl and 8-10-membered bicyclic heteroaryl.

As used herein, the term "5-6-membered heteroaryl" means a monocyclic aromatic group with a total of 5 or 6 atoms in the ring wherein from 1 to 4 of those atoms are each independently selected from N, O and S. Preferred groups have 1, 2 or 3 atoms in the ring which are each independently selected from N, O and S. Examples of 5-membered heteroaryl groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Examples of 6-membered heteroaryl groups include pyridinyl, pyrimidyl, pyrazinyl, pyridazinyl and triazinyl.

"Pyrrolyl" as used herein includes pyrrol-1-yl, pyrrol-2-yl and pyrrol-3-yl.

"Furanyl" (also called "furyl") as used herein includes furan-2-yl and furan-3-yl (also called 2-furyl and 3-furyl). Furan-2-yl is preferred.

"Thienyl" (also called "thiophenyl") as used herein includes thien-2-yl and thien-3-yl (also called 2-thiophenyl and 3-thiophenyl).

"Pyrazolyl" as used herein includes pyrazol-1-yl, pyrazol-3-yl, pyrazol-4-yl and pyrazol-5-yl (also called 1-pyrazole, 3-pyrazole, 4-pyrazole and 5-pyrazole). Pyrazol-1-yl is preferred.

"Imidazolyl" as used herein includes imidazol-1-yl, imidazol-2-yl, imidazol-4-yl and imidazol-5-yl. Imidazol-1-yl and imidazol-2-yl are preferred.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl (also called 2-thiazolyl, 4-thiazolyl and 5-thiazolyl).

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-2-yl, 1,2,3-triazol-4-yl, 1,2,3-triazol-5-yl, 1,2,4-triazol-1-yl, 1,2,4-triazol-3-yl and 1,2,4-triazol-5-yl. 1,2,3-triazol-1-yl, 1,2,3-triazol-2-yl and 1,2,4-triazol-1-yl are preferred.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" (also called "pyridyl") as used herein includes pyridin-2-yl, pyridin-3-yl and pyridin-4-yl (also called 2-pyridyl, 3-pyridyl and 4-pyridyl).

"Pyrimidyl" as used herein includes pyrimid-2-yl, pyrimid-4-yl, pyrimid-5-yl and pyrimid-6-yl.

"Pyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

As used herein, the term "8-10-membered bicyclic heteroaryl" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaryl groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaryl groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaryl groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" (also called "benzothiophenyl") as used herein includes benzothien-2-yl, benzothien-3-yl, benzothien-4-yl, benzothien-5-yl, benzothien-6-yl and benzothien-7-yl (also called 2-benzo[b]thiophenyl, 3-benzo[b]thiophenyl, 4-benzo[b]thiophenyl, 5-benzo[b]thiophenyl, 6-benzo[b]thiophenyl and 7-benzo [b]thiophenyl).

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl. Indazol-1-yl is preferred.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl. Benzimidazol-1-yl is preferred "1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl. Benzotriazol-1-yl is preferred.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

As used herein, the term "$C_1$-$C_4$ alkylheteroaryl" refers to a $C_1$-$C_4$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_4$ alkylheteroaryl include thiophenylmethyl, thiophenylethyl, furanylmethyl, furanylethyl, imidazolylmethyl, imidazolylethyl, triazolylmethyl and triazolylethyl.

As used herein, the term "$C_1$-$C_6$ alkylheteroaryl" refers to a $C_1$-$C_6$ alkyl group as defined herein wherein one of the hydrogens is replaced by a heteroaryl substituent as defined herein which replacement can be at any site on the alkyl chain, and includes thiophenylmethyl, thiophenylethyl, thiophenylpropyl, thiophenylbutyl furanylmethyl, furanylethyl, furanylpropyl, furanylbutyl, pyrrolylmethyl, pyrrolylethyl, pyrrolylpropyl, pyrrolylbutyl, imidazolylmethyl, imidazolylethyl, imidazolylpropyl, imidazolylbutyl, triazolylmethyl, triazolylethyl, triazolylpropyl, triazolylbutyl, pyridinylmethyl, pyridinylethyl, pyridinylpropyl, pyridinylbutyl, quinolinylmethyl, quinolinylethyl, quinolinylpropyl and quinolinylbutyl. Preferred $C_1$-$C_6$ alkylheteroaryl include thiophenylmethyl, thiophenylethyl, furanylmethyl, furanylethyl, imidazolylmethyl, imidazolylethyl, triazolylmethyl and triazolylethyl.

As used herein the term "5-8 membered carbocyclic ring" include cyclopentenyl, cyclohexenyl, phenyl, cycloheptenyl and cyclooctenyl. Preferable carbocyclic rings have from 5 to 6 carbon atoms, such as cyclopentene, cyclohexene and phenyl.

As used herein the term "heterocycle" refers to a saturated ring having from 4 to 8 atoms and preferably 5 or 6 atoms which incorporate the N atom of R9, optionally having one or two additional heteroatoms selected from oxygen, sulfur and nitrogen, the remaining atoms being carbon.

As used herein the term "4-8 membered heterocycle" include azetidine, pyrolidine, piperidine, piperizine, morpholine and thiomorpholine.

The compounds of the present invention may be chiral, and it is intended that any enantiomers, as separated, pure or partially purified enantiomers or racemic mixtures thereof are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The compounds of formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 - E^2} \times 100$$

wherein E1 is the amount of the first enantiomer and E2 is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee o greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "Enantiomers. Racemates, and Resolutions," John Wiley and Sons, Inc., 1981, and E. L. Eliel and S. H. Wilen, "Stereochemistry of Organic Compounds," (Wiley-Interscience 1994). Examples of resolutions include recrystallization techniques or chiral chromatography.

Formula I, Ia, Ib and Ic show the structure of the compounds of the present invention without preferred stereochemistry. Preferred stereochemistry of the compounds of the present invention are indicated by the compounds of formula II, IIa, IIb and IIc. Preferred compounds of the present invention include 2-[(2S,3R)-3-Amino-2-hydroxy-4-(2,4,5-trifluoro-phenyl)-butyl]-N-tert-butyl-4-chloro-benzamide, 2-[(2S,3R)-3-Amino-2-hydroxy-4-(2,4,5-trifluoro-phenyl)-butyl]-N-tert-butyl-4-methyl-benzamide, 2-[(2S,3R)-3-Amino-4-(2,5-difluoro-phenyl)-2-hydroxy-butyl]-N-tert-butyl-4-chloro-benzamide, 2-[(2S,3R)-3-Amino-4-(2-fluoro-phenyl)-2-methoxy-butyl]-N-tert-butyl-4-chloro-benzamide, 2-[(2S,3R)-3-Amino-4-(2-fluoro-phenyl)-2-hydroxy-butyl]-N-tert-butyl-4-fluoro-benzamide, 2-[(2S,3R)-3-Amino-4-(2-fluoro-phenyl)-2-hydroxy-butyl]-N-tert-butyl-4-methoxy-benzamide, 2-[(2S,3R)-3-Amino-4-(2-fluoro-phenyl)-2-hydroxy-butyl]-N-tert-butyl-5chloro-benzamide, 2-[(2S,3R)-3-Amino-4-(2-fluoro-phenyl)-2-hydroxy-butyl]-N-tert-butyl-6-methyl-benzamide, 2-[(2S,3R)-3-Amino-4-(2-fluoro-phenyl)-2-hydroxy-butyl]-N-tert-butyl-5-methyl-benzamide, 2-[(2S,3R)-3-Amino-4-(2-fluoro-phenyl)-2-hydroxy-butyl]-N-tert-butyl-6-chloro-benzamide, 2-[(2S,3R)-3-Amino-4-(2-fluoro-phenyl)-2-hydroxy-butyl]-N-tert-butyl-3-methyl-benzamide and 2-[(2S,3R)-3-Amino-4-(2-fluoro-phenyl)-2-hydroxy-butyl]-N-tert-butyl-3-chloro-benzamide or a pharmaceutically acceptable salt thereof.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts," J. Pharm. Sci., 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts. Typical pharmaceutical salts include those salts prepared by reaction of the compounds of formula I with an inorganic or organic acid. Such salts are known as acid addition salts. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts.

Preferred pharmaceutical acid addition salts are hydrochloric acid and the like.

The compounds of the present invention may form solvates with standard low molecular weight solvents using methods well known to the person skilled in the art. Such solvates are also contemplated as being within the scope of the present invention.

The compounds of the present invention are useful in the treatment or prevention of the following conditions or diseases: hyperglycaemia, low glucose tolerance, insulin resistance, obesity, lipid disorders, dyslipidemia, hyperlipidemia, hypertriglyceridema, hypercholesterolemia, low HDL levels, high LDL levels, atherosclerosis and its sequelae, vascular restenosis, irritable bowel syndrome, inflammatory bowel disease, Crohn's disease, ulcerative colitis, other inflammatory conditions, pancreatitis, abdominal obesity, neurodegenerative disease, retinopathy, nephropathy, neuropathy, Syndrome X, polycystic ovarian syndrome, Type II diabetes, growth hormone deficiency, neutropenia, neuronal disorders, tumor metastasis, benign prostatic hypertrophy, hypertension, osteoporosis and other conditions that may be treated or prevented by inhibition of DPP-IV.

In a further aspect of the invention the present compounds are administered in combination with one or more further active substances. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations.

Thus, in a further aspect of the invention the present compounds may be administered in combination with one or more antidiabetics. Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28} Pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1, GLP-1 mimetics and GLP-1 receptor agonists such as those disclosed in WO00/42026 and WO0059887, other DPP-IV inhibitors such as isoleucine thiazolidide (P32/98), NVP-DPP-728, LAF 237, P93/01, MK-0431 (Sitagliptin), and BMS 477118, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069

In another aspect of the invention, the present compounds are administered in combination with insulin or an insulin analogue or derivative, such as $N^{\epsilon B29}$-tetradecanoyl des (B30) human insulin, $Asp^{B28}$ human insulin, $Lys^{B28} Pro^{B29}$ human insulin, Lantus®, or a mix preparation comprising one or more of these.

In a further aspect of the invention the present compounds are administered in combination with a sulphonylurea such as glibenclamide, glipizide, tolbautamide, chloropamidem, tolazamide, glimepride, glicazide and glyburide.

In another aspect of the invention the present compounds are administered in combination with a biguanidine for example metformin.

In yet another aspect of the invention the present compounds are administered in combination with a meglitinide for example repaglinide or nateglinide.

In still another aspect of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another aspect of the invention the present compounds may be administered in combination with an insulin sensitizer for example such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (-)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further aspect of the invention the present compounds are administered in combination with an α-glucosidase inhibitor for example voglibose, emiglitate, miglitol or acarbose.

In another aspect of the invention the present compounds are administered in combination with an agent acting on the ATP-dependent potassium channel of the β- cells for example tolbutamide, glibenclamide, glipizide, glicazide, BTS-67582 or repaglinide.

In yet another aspect of the invention the present compounds may be administered in combination with nateglinide.

In still another aspect of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate oratorvastin.

In still another aspect of the invention the present compounds are administered in combination with compounds lowering food intake.

In another aspect of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further aspect of the invention the present compounds may be administered in combination with one or more anti-obesity agents or appetite regulating agents. Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant).

In another aspect of the invention the antiobesity agent is dexamphetamine or amphetamine.

In another aspect of the invention the antiobesity agent is leptin.

In another aspect of the invention the antiobesity agent is fenfluramine or exfenfluramine.

In still another aspect of the invention the antiobesity agent is sibutramine.

In a further aspect of the invention the antiobesity agent is orlistat.

In another aspect of the invention the antiobesity agent is mazindol or phentermine.

In still another aspect of the invention the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of formula I can be prepared by one of ordinary skill in the art following a variety of procedures, some of which are illustrated in the procedures and schemes set forth below. The particular order of steps required to produce the compounds of formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumina.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "deprotection" of suitable protecting groups to be used by the skilled artisan.

The skilled artisan will appreciate that not all substituents are compatible with all reaction conditions. These compounds may be protected or modified at a convenient point in the synthesis by methods well known in the art.

The compounds of the present invention may be prepared as is shown in the following reaction schemes.

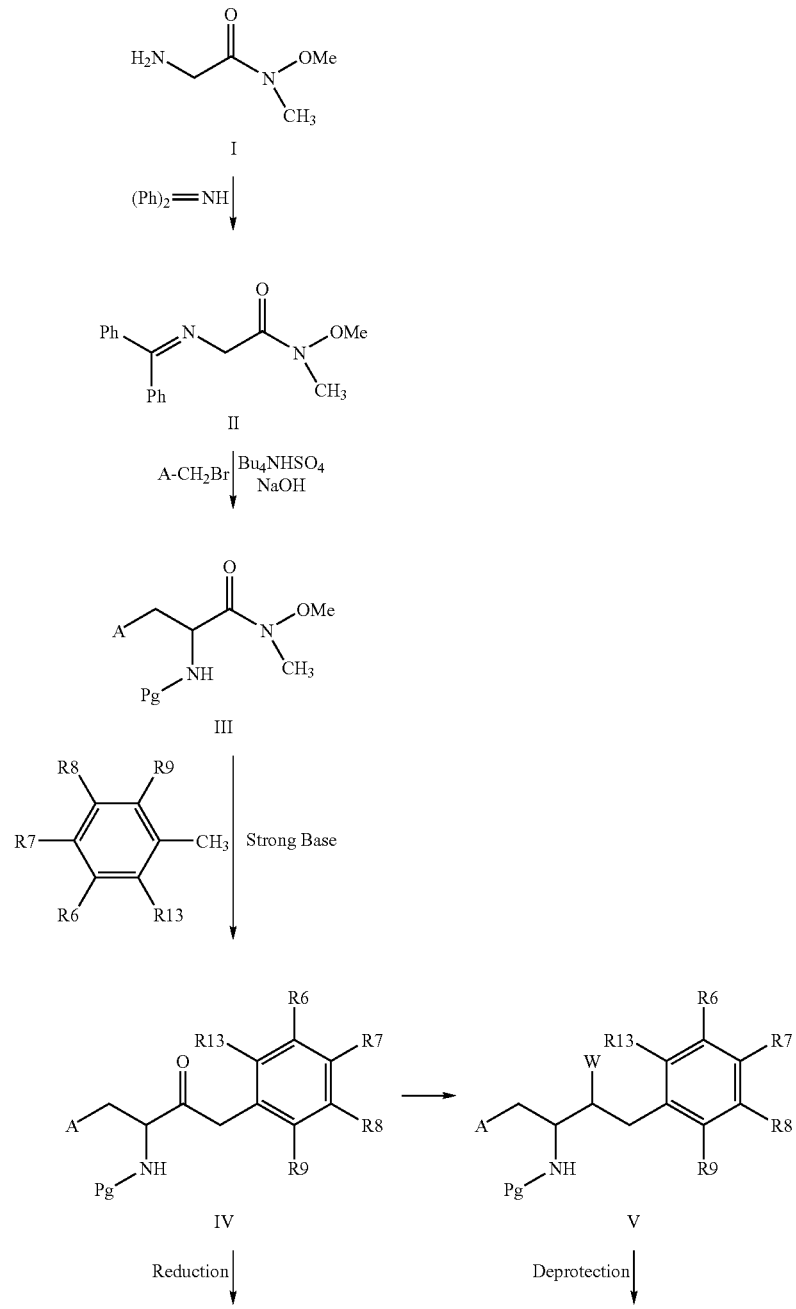

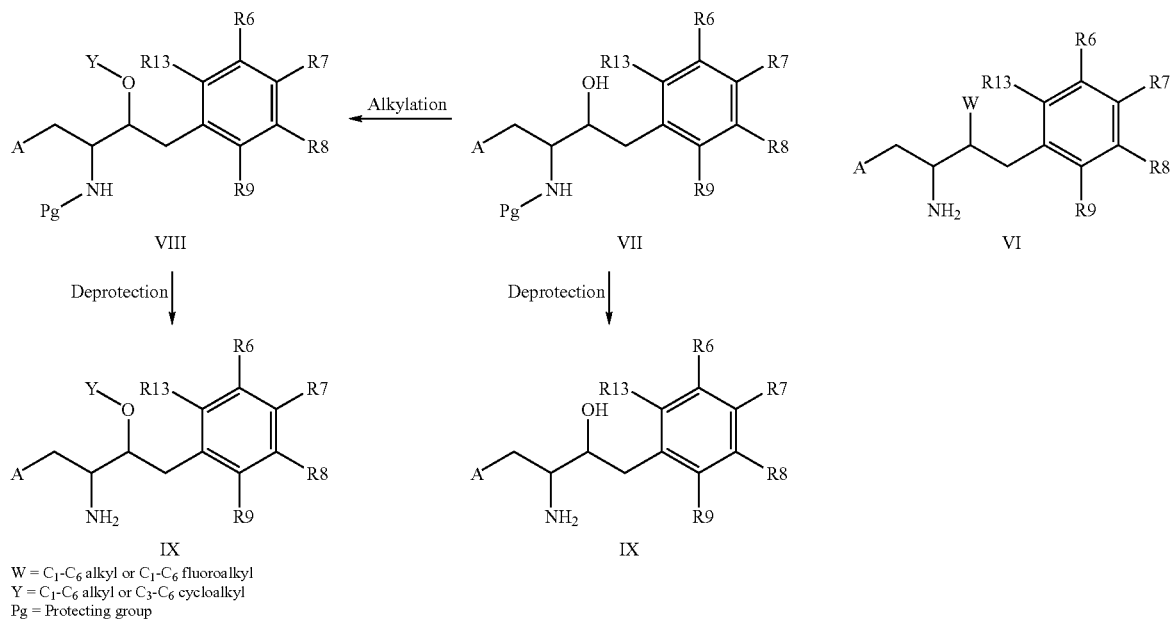

W = $C_1$-$C_6$ alkyl or $C_1$-$C_6$ fluoroalkyl
Y = $C_1$-$C_6$ alkyl or $C_3$-$C_6$ cycloalkyl
Pg = Protecting group The intermediate III of Scheme I is prepared according to the method described in Acc. Chem. Res. 2004, 37, 506-517.

The Weinreb amides as intermediate I of Scheme I and III* of Scheme II are prepared according to the method described in Tetrahedron Letters, 1981, vol 22, 3815.

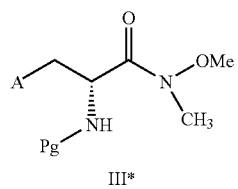

III*

*-indicates chiral

Scheme II

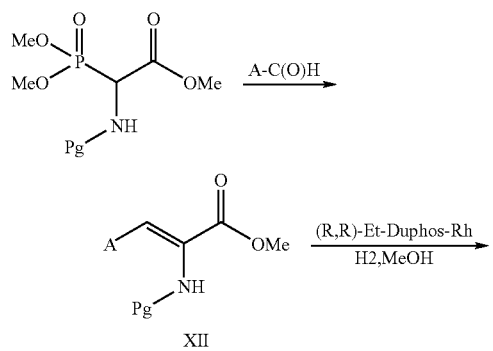

Scheme III

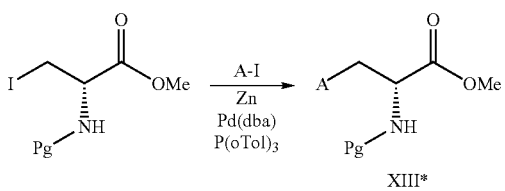

The intermediate XIII* of Scheme III is prepared according to the method described in Organic Syntheses, 2004, vol 81, 77-87.

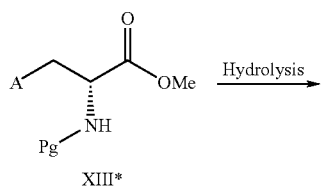

Scheme IV

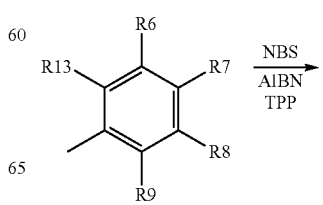

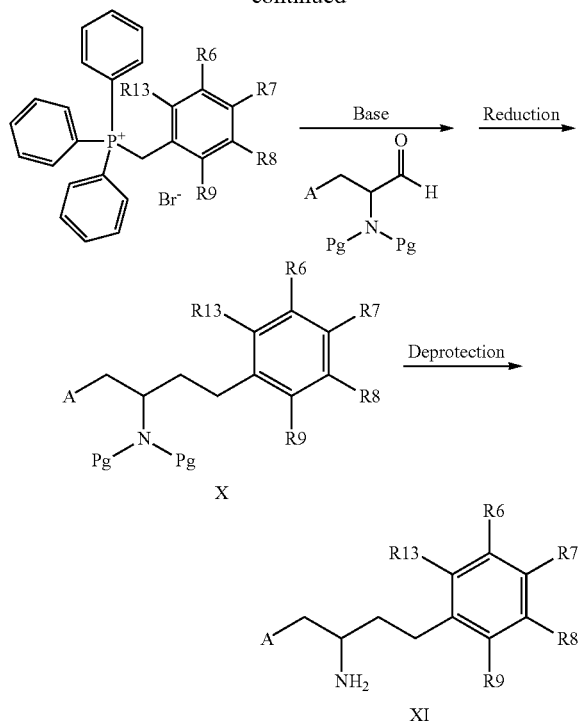

Experimental Section

Abbreviations used follow IUPAC-IUB nomenclature. Additional abbreviations are aq., aqueous; equiv, (molar) equivalent; HPLC, high-performance liquid chromatography; THF, tetrahydrofuran; HOAc, acetic acid; DMSO, dimethyl sulfoxide (perdeuterated if for NMR); EtOAc, ethyl acetate; EtOH, ethanol; MeOH, methanol; DNM, dimethylformamide; DBU, 1,8-diazabicyclo[5.4.0]undec-7-ene; HOBT, 1-hydroxy benzotriazole; EDCI, 1-(3-dimethylaminopropyl)-3-ethylcarbodiimide hydrochloride; LDA, lithium diisopropylamide; TMEDA, N,N,N',N'-tetramethylethylenediamine; AIBN, 2,2'-azobisisobutyronitrile; Boc, tertiary-butyloxy-carbonyl; Cbz, benzyloxy-carbonyl; MS, electrospray mass spectrum; TFA, trifluoroacetic acid; (R,R)-Et-DUPHOS-Rh, bis-((2R,5R)-2,5-diethylphospholano)-benzene-(cyclooctadiene)-rhodium(I) tetrafluoroborate or trifluoromethanesulfonate salt. All solution concentrations are expressed as % volume/% volume unless otherwise stated. Reagents were obtained from a variety of commercial sources. $^1$HNMR means a proton magnetic resonance spectrum was obtained.

General Reaction Procedures

General Procedure 1—Formation of Weinreb Amide

To a solution of protected amino acid (1 equiv), 1-hydroxybenzotriazole (1.5 equiv), N,O-dimethylhydroxylamine hydrochloride (1.1 equiv) and N,N-diisopropylethylamine (3 equiv) in DMF (0.1-0.5M) is added 1-(3-dimethylaminopropyl)-3-ethylcarbodiimide hydrochloride (1.5 equiv) and the reaction is allowed to stir overnight. The reaction is quenched with saturated NaHCO$_3$ and the product is extracted into a suitable organic solvent. The combined organic layers are washed with brine, dried over magnesium sulfate or sodium sulfate, filtered and are concentrated under reduced pressure to afford a crude residue. Purification by silica gel flash column chromatography provides the product.

General Procedure 2—Addition of 2-methyl-benzene Derivative to Weinreb Amides

An oven-dried three-neck flask fitted with a thermometer, mechanical stirrer, and nitrogen inlet is charged with a 2-methyl-benzene derivative (3 equiv) in THF (0.1-0.5M) and the flask is cooled to −78° C. To the solution is added sec-BuLi dropwise such that the internal temperature remains below −60° C. The reaction is then allowed to stir at −78° C. for an additional 1-3 hours. A solution of Weinreb amide (1 equiv) in THF (0.1-1M) is added dropwise to the reaction and the reaction is allowed to continue stirring at −78° C. for an additional 0.5-2 hours. The reaction is then quenched at −78° C. by addition of either acetic acid or 2M NaHSO4 such that the resultant mixture is pH<7. The quenched reaction mixture is allowed to warm to room temperature and the product is extracted into a suitable organic solvent. The combined organic layers are washed with brine, dried over magnesium sulfate or sodium sulfate, filtered and are concentrated concentrated under reduced pressure to afford a crude residue. Purification by silica gel flash column chromatography provides the product.

General Procedure 3—Ketone Reduction

To a solution of ketone (1 equiv) in absolute ethanol (0.1-0.5M) at 0° C. is added sodium borohydride (1-5 equiv) portion wise under a stream of nitrogen. The reaction is then allowed to warm to room temperature and is stirred for an additional 1-16 hours. The combined organic layers are washed with brine, dried over magnesium sulfate or sodium sulfate, filtered and are concentrated concentrated under reduced pressure to afford a crude residue. Purification by silica gel flash column chromatography provides the product.

General Procedure 4—Amide Coupling

To a solution of carboxylic acid (1 equiv) in DMF or CH$_2$Cl$_2$ (0.1-0.3M) is added tert-butylamine (1.5 equiv), HOBt (1.5 equiv), EDCI (1.5 equiv) and diisopropylethylamine (8-10 equiv). The reaction is allowed to stir at room temperature for 6-16 hours after which time it is poured into water and is extracted with a suitable organic solvent. The combined organic layers are washed with brine, dried over magnesium sulfate or sodium sulfate, filtered and are concentrated under reduced pressure to afford a crude residue. Purification by silica gel flash column chromatography provides the product.

General Procedure 5—Preparation of Enantiomerically Enriched Alanine Derivatives To a slurry of (R)-benzyloxycarbonylamino-(dimethoxyphosphoryl)-acetic acid methyl ester (1.06 equiv) in dichloromethane (1-3M) at 0° C. is slowly added DBU (1.1 equiv). The resultant solution is then allowed to stir at room temperature for 30 minutes after which time it is recooled to 0° C. A solution of the appropriately substituted benzaldehyde (1 equiv) in dichloromethane (2-5M) is then slowly added to the solution after which time the reaction is allowed to warm and stir at room temperature for 4 hours. The reaction is then poured into an ice-chilled solution of 1N aqueous H$_2$SO$_4$ and then diluted with EtOAc. The organic layer is washed with water and brine, dried over magnesium sulfate or sodium sulfate, filtered and is concentrated under reduced pressure to afford a crude residue. Purification by silica gel flash column chromatography provides the Horner Emmons product. This product (1 equiv) is then dissolved in methanol (0.2-0.5 M) and bis-((2R,5R)-2,5-diethylphospholano)-benzene-(cyclooctadiene)-rhodium(I) tetrafluoroborate or trifluoromethanesulfonate salt (0.002-0.1 equiv) is added. The mixture is then stirred at room temperature under hydrogen at 50-100 psi for 4-24 hours after which time the flask is vented and the reaction is filtered through a pad of celite. Concentration of the filtrate gives the product.

General Procedure 6—Ester Hydrolysis

To a solution of ester (1 equiv) in a solution of 2:1 dioxane:water (0.1-0.5 M) is added lithium hydroxide (1-10 equiv). After stirring for 1-24 hours, water is added and the solution is adjusted to pH 5-6 by addition of an aqueous protic acid. The product is then extracted into a suitable organic solvent which is then dried over sodium or magnesium sulfate, is filtered, and is concentrated under reduced pressure to give the product.

General Deprotection Procedure 1

Into a solution of Boc-protected amine in a suitable non-protic organic solvent (0.01-0.5M) at 0° C.-room temperature is bubbled HCl gas for 5-15 minutes. Removal of the solvent under reduced pressure provides the product.

General Deprotection Procedure 2

To a solution of cbz-protected amine in EtOH (0.1-0.5M) is added Pd/C (0.1-1 equiv) and the mixture is shaken under hydrogen at 60 psi for 2-24 hours.

General Deprotection Procedure 3

To a solution of Boc-protected amine in dichloromethane (0.1-1M) is added trifluoroacetic acid. The reactions are stirred for 1-20 hours after which time the reactions are concentrated under reduced pressure. Saturated $NaHCO_3$ is added and the product is extracted into dichloromethane. The combined organic phases are concentrated under reduced pressure and excess of a 1N solution of HCl in ether or ethyl acetate is added and the product is isolated by centrifugation.

General Deprotection Procedure 4

To the starting Boc-protected amine is added an excess amount of a 5% solution of trifluoroacetic acid in dichloromethane. The reaction is stirred for 10-20 hr after which time the reaction mixture is either concentrated under reduced pressure or is added to saturated NaHCO3 and is extracted into dichloromethane which is then concentrated to provide a crude residue.

General Deprotection Procedure 5

To the starting Boc-protected amine is added an excess amount of a 1N solution of HCl in dioxane. The reaction is stirred for 1-5 hr after which time the reaction mixture is concentrated under reduced pressure to provide a crude residue.

General Purification Methods

Purification Method 1

The crude product is purified by preparative HPLC on an Xterra™ RP18 (30×300 mm) column at 30° C. and a flow of 10 ml/min. The elution system is or consists of an isocratic gradient of 10:90 (acetonitrile: (0.1% HCl in $H_2O$)) for 1-5 min followed by a linear gradient from 10:90 (acetonitrile: (0.1% HCl in $H_2O$)) to 30:70 (acetonitrile:(0.1% HCl in $H_2O$)) over 20 min. The fractions are concentrated to give the purified compound.

Purification Method 2

The crude product is purified by preparative HPLC on an Xterra™ RP18 (30×300 mm) column at 30° C. and a flow of 10 ml/min. The elution system is or consists of an isocratic gradient of 0:100 (acetonitrile:(0.1% HCl in $H_2O$)) for 1-5 min followed by a linear gradient from 0:100 (acetonitrile: (0.1% HCl in $H_2O$)) to 70:30 (acetonitrile:(0.1% HCl in $H_2O$)) over 25 min. The fractions are concentrated to give the purified compound.

Purification Method 3

The product is purified by HPLC chiral separation (Column: 46×15 cm chiralpak AD-H; Eluent: 10:90:0.2 (isopropyl alcohol:heptanes:dimethylethylamine); Flow: 0.6 mL/min at UV 279 nm) affords enantiomerically enriched compound. The fractions are concentrated under reduced pressure and the resultant residue is treated with excess of a 0.1-2N solution of HCl in an appropriate solvent. Filtration or concentration gives the compound as the HCl salt.

Preparation of Common Intermediates

Intermediate 1

[(R)-1-(Methoxy-methyl-carbamoyl)-2-(2,4,5-trifluoro-phenyl)-ethyl]-carbamic acid benzyl ester

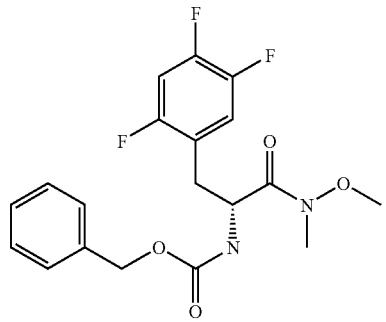

Step A (R)-2-Benzyloxycarbonylamino-3-(2,4,5-trifluoro-phenyl)-propionic acid methyl ester Using general procedure 5 with 2,4,5-trifluorobenzaldehyde (12.7 g, 79 mmol) gives the title compound.

$^1$HNMR

MS (m/e): 368 (M+1)

Step B (R)-2-Benzyloxycarbonylamino-3-(2,4,5-trifluoro-phenyl)-propionic acid

Using general procedure 6 with (R)-2-benzyloxycarbonylamino-3-(2,4,5-trifluoro-phenyl)-propionic acid methyl ester (5.0 g, 14 mmol) gives the title compound.

$^1$HNMR

MS (m/e): 352 (M+1)

Step C (R)-[1-(Methoxy-methyl-carbamoyl)-2-(2,4,5-trifluoro-phenyl)-ethyl]-carbamic acid benzyl ester Using general procedure 1 with (R)-3-benzyloxycarbonylamino-2-oxo-4-(2,4,5-trifluoro-phenyl)-butyric acid (3.8 g, 11 mmol) gives the title compound.

$^1$HNMR

MS (m/e): 397 (M+1)

Intermediate 2

[(R)-1-(Methoxy-methyl-carbamoyl)-2-(2,4,5-trifluoro-phenyl)-ethyl]-carbamic acid tert-butyl ester

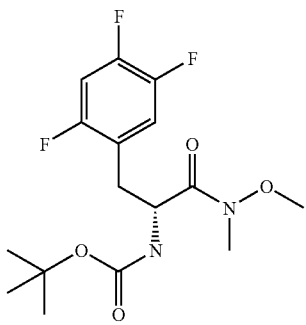

To a solution of [(R)-1-(methoxy-methyl-carbamoyl)-2-(2,4,5-trifluoro-phenyl)-ethyl]-carbamic acid benzyl ester (10.5 g, 27 mmol), di-tert-butyl dicarbonate (7.f g, 34 mmol) in 375 mL of methanol is added 500 mg of 10% Pd/C. The suspension is stirred under hydrogen at atmospheric pressure for 16 hours after which time the crude mixture is filtered through a pad of celite and the filtrate is concentrated under reduced pressure. Purification of the resultant residue by silica gel flash column chromatography provides the title compound.

$^1$HNMR

MS (m/e): 363 (M+1)

Intermediate 3

[(R)-2-(2,5-Difluoro-phenyl)-1-(methoxy-methyl-carbamoyl)-ethyl]-carbamic acid benzyl ester

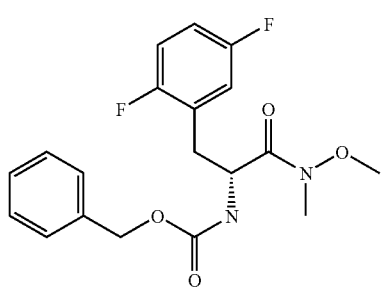

Step A (R)-2-Benzyloxycarbonylamino-3-(2,5-difluoro-phenyl)-propionic acid methyl ester Using general procedure 5 with 2,5-difluorobenzaldehyde (200 g, 1.4 mol) gives the title compound.

$^1$HNMR

MS (m/e): 350 (M+1)

Step B (R)-2-Benzyloxycarbonylamino-3-(2,5-difluoro-phenyl)-propionic acid

Using general procedure 6 with (R)-2-benzyloxycarbonylamino-3-(2,5-difluoro-phenyl)-propionic acid methyl ester (60 g, 170 mol) gives the title compound.

$^1$HNMR

MS (m/e): 334 (M−1)

Step C

[(R)-2-(2,5-Difluoro-phenyl)-1-(methoxy-methyl-carbamoyl)-ethyl]-carbamic acid benzyl ester Using general procedure 1 with (R)-3-benzyloxycarbonylamino-2-oxo-4-(2,5-difluoro-phenyl)-butyric acid (20 g, 61 mmol) gives the title compound.

$^1$HNMR mass spectrum (m/e): 379 (M+1)

Intermediate 4

[(R)-2-(2,5-Difluoro-phenyl)-1-(methoxy-methyl-carbamoyl)-ethyl]-carbamic acid tert-butyl ester

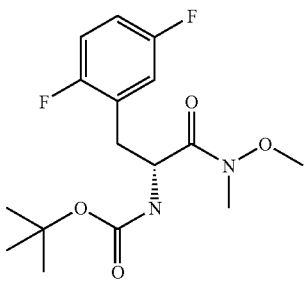

Step A (R)-2-tert-Butoxycarbonylamino-3-(2,5-difluoro-phenyl)-propionic acid methyl ester Using general procedure 5 with 2,5-difluorobenzaldehyde (5.5 g, 39 mmol) gives the title compound.

$^1$HNMR

MS (m/e): 216 (M+1−C$_4$H$_9$)

Step B (R)-2-tert-Butoxycarbonylamino-3-(2,5-difluoro-phenyl)-propionic acid

Using general procedure 6 with (R)-2-tert-butoxycarbonylamino-3-(2,5-difluoro-phenyl)-propionic acid methyl ester (23 g, 72 mmol) gives the title compound.

$^1$HNMR

MS (m/e): 300 (M−1)

Step C

[(R)-2-(2,5-Difluoro-phenyl)-1-(methoxy-methyl-carbamoyl)-ethyl]-carbamic acid tert-butyl ester Using general procedure 1 with (R)-2-tert-Butoxycarbonylamino-3-(2,5-difluoro-phenyl)-propionic acid (20 g, 65 mmol) gives the title compound.

$^1$HNMR mass spectrum (m/e): 289 (M+1-C$_4$H$_9$)

Intermediate 5

[(R)-2-(2-Fluoro-phenyl)-1-(methoxy-methyl-carbamoyl)-ethyl]-carbamic acid tert-butyl ester

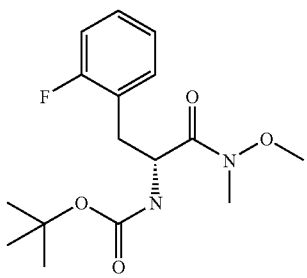

Using general procedure 1 with (R)-2-tert-butoxycarbonylamino-3-(2-fluoro-phenyl)-propionic acid (15g, 53mmol) gives the title compound.
¹HNMR
MS (m/e): 227 (M+1)

Intermediate 6

N-tert-Butyl-4-chloro-2-methyl-benzamide

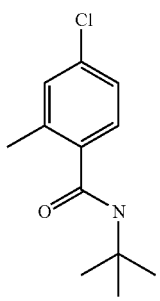

Using general procedure 4 with 4-chloro-2-methylbenzoic acid (10.0 g, 58.8 mmol) gives the title compound.
¹HNMR
mass spectrum (m/e): 226 (M+1)

Intermediate 7

N-tert-Butyl-2,4-dimethyl-benzamide

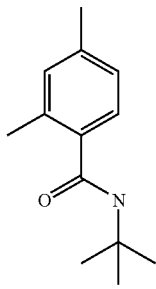

Using general procedure 4 with 2,4-dimethylbenzoic acid (6.6 g, 44 mmol) followed by purification using silica gel flash column chromatography gives the title compound.
¹HNMR
mass spectrum (m/e): 206 (M+1)

Intermediate 8

N-tert-Butyl-4-fluoro-2-methyl-benzamide

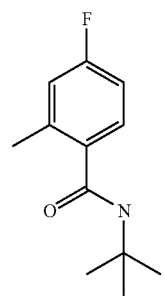

Using general procedure 4 with 4-fluoro-2-methylbenzoic acid (10.0 g, 65 mmol) followed by purification using silica gel flash column chromatography gives the title compound.
¹HNMR
mass spectrum (m/e): 210 (M+1)

Intermediate 9

N-tert-Butyl-4-methoxy-2-methyl-benzamide

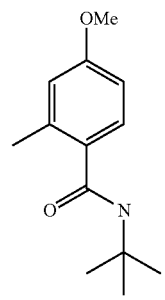

Using general procedure 4 with 4-methoxy-2-methylbenzoic acid (5.0 g, 30 mmol) followed by purification using silica gel flash column chromatography gives the title compound.
¹HNMR
mass spectrum (m/e): 222 (M+1)

Intermediate 10

N-tert-Butyl-5-chloro-2-methyl-benzamide

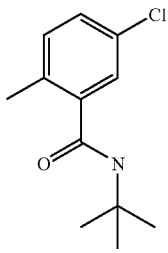

Using general procedure 2 with 4-chloro-2-methylbenzoic acid (5.0 g, 29 mmol) followed by purification using silica gel flash column chromatography gives the title compound.
¹HNMR
mass spectrum (m/e): 226 (M+1)

Intermediate 11

N-tert-Butyl-2-chloro-6-methyl-benzamide

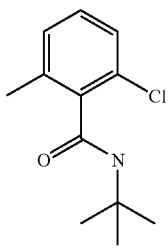

Using general procedure 2 with 2-chloro-6-methyl-benzoic acid (5.0 g, 29 mmol) followed by purification using silica gel flash column chromatography gives the title compound.
¹HNMR
mass spectrum (m/e): 226 (M+1)

Intermediate 12

N-tert-Butyl-2,6-dimethyl-benzamide

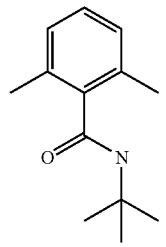

Using general procedure 2 with 2,6-dimethylbenzoic acid (8.8 g, 59 mmol) followed by purification using silica gel flash column chromatography gives the title compound.
¹HNMR
mass spectrum (m/e): 206 (M+1)

Intermediate 13

N-tert-Butyl-2,5-dimethyl-benzamide

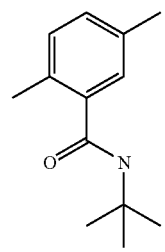

Using general procedure 2 with 2,5-dimethylbenzoic acid (5.0 g, 33 mmol) followed by purification using silica gel flash column chromatography gives the title compound.
¹HNMR
mass spectrum (m/e): 206 (M+1)

Preparation of DPIV Inhibitors

EXAMPLE 1

2-[(2S,3R)-3-Amino-2-hydroxy-4-(2,4,5-trifluoro-phenyl)-butyl]-N-tert-butyl-4-chloro-benzamide Hydrochloride

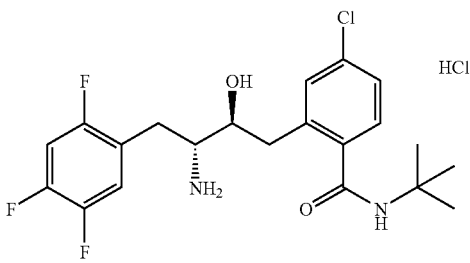

Step A

[(R)-3-(2-tert-Butylcarbamoyl-5-chloro-phenyl)-2-oxo-1-(2,4,5-trifluoro-benzyl)-propyl]-carbamic acid tert-butyl ester Using general procedure 2 with [(R)-1-(methoxy-methyl-carbamoyl)-2-(2,4,5-trifluoro-phenyl)-ethyl]-carbamic acid tert-butyl ester (1.4 g, 3.4 mmol) and N-tert-butyl-4-chloro-2-methyl-benzamide (2.3 g, 10 mmol) followed by purification by silica gel flash column chromatography gives the title compound.
¹HNMR
MS (m/e): 527 (M+1)

Step B

[(1R,2S)-3-(2-tert-Butylcarbamoyl-5-chloro-phenyl)-2-hydroxy-1-(2,4,5-trifluoro-benzyl)-propyl]-carbamic acid tert-butyl ester Using general procedure 3 with [(R)-3-(2-tert-butylcarbamoyl-5-chloro-phenyl)-2-oxo-1-(2,4,5-trifluoro-benzyl)-propyl]-carbamic acid tert-butyl ester (0.68 g, 1.3 mmol)

followed by purification by silica gel flash column chromatography gives the title compound.
¹HNMR
MS (m/e): 528 (M+1)
Step C 2-[(2S,3R)-3-Amino-2-hydroxy-4-(2,4,5-trifluoro-phenyl)-butyl]-N-tert-butyl-4-chloro-benzamide Hydrochloride Using general deprotection procedure 1 with [(1R,2S)-3-(2-tert-butylcarbamoyl-5-chloro-phenyl)-2-hydroxy-1-(2,4,5-trifluoro-benzyl)-propyl]-carbamic acid tert-butyl ester (0.41 g, 0.78 mmol) gives the title compound.
¹HNMR (300 MHz, CD₃OD) δ 7.45-7.15 (m, 5H), 4.14-3.99 (m, 1H), 3.61-3.48 (m, 1H), 3.26-3.12 (m, 1H), 3.02-2.88 (m, 3H), 1.44 (s, 9H).
MS (m/e): 429 (M+1)

EXAMPLE 2

2-[(2S,3R)-3-Amino-2-hydroxy-4-(2,4,5-trifluoro-phenyl)-butyl]-N-tert-butyl-4-methyl-benzamide Hydrochloride

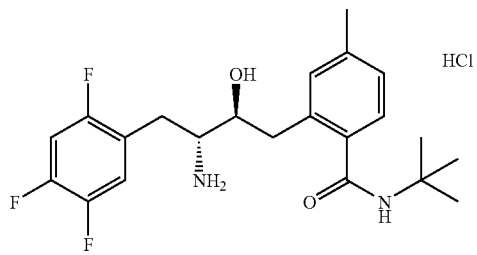

Step A

[(R)-3-(2-tert-Butylcarbamoyl-5-methyl-phenyl)-2-oxo-1-(2,4,5-trifluoro-benzyl)-propyl]-carbamic acid tert-butyl ester Using general procedure 2 with [(R)-1-(methoxy-methyl-carbamoyl)-2-(2,4,5-trifluoro-phenyl)-ethyl]-carbamic acid tert-butyl ester (1.4 g, 4.1 mmol) and N-tert-Butyl-2,4-dimethyl-benzamide (2.5 g, 12 mmol) followed by purification by silica gel flash column chromatography gives the title compound.
¹HNMR
MS (m/e): 507 (M+1)
Step B

[(1R,2S)-3-(2-tert-Butylcarbamoyl-5-methyl-phenyl)-2-hydroxy-1-(2,4,5-trifluoro-benzyl)-propyl]-carbamic acid tert-butyl ester Using general procedure 3 with [(R)-3-(2-tert-butylcarbamoyl-5-methyl-phenyl)-2-oxo-1-(2,4,5-trifluoro-benzyl)-propyl]-carbamic acid tert-butyl ester (1.8 g, 3.5 mmol) followed by purification by silica gel flash column chromatography gives the title compound.
¹HNMR
MS (m/e): 509 (M+1)

Step C

2-[(2S,3R)-3-Amino-2-hydroxy-4-(2,4,5-trifluoro-phenyl)-butyl]-N-tert-butyl-4-methyl-benzamide Hydrochloride Using general deprotection procedure 1 with [(1R,2S)-3-(2-tert-Butylcarbamoyl-5-methyl-phenyl)-2-hydroxy-1-(2,4,5-trifluoro-benzyl)-propyl]-carbamic acid tert-butyl ester (1.1 g, 2.2 mmol) gives the title compound.
¹HNMR (300 MHz, CD₃OD) δ 7.33-7.21 (m, 5H), 4.11-3.96 (m, 1H), 3.62-3.48 (m, 1H), 3.24-3.10 (m, 1H), 3.04-2.82 (m, 3H), 2.35 (s, 3H), 1.45 (s, 9H).
MS (m/e): 409 (M+1).

EXAMPLE 3

2-[(2S,3R)-3-Amino-4-(2,5-difluoro-phenyl)-2-hydroxy-butyl]-N-tert-butyl-4-chloro-benzamide Hydrochloride

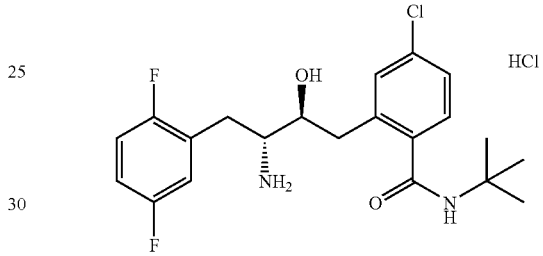

Step A

[(R)-3-(2-tert-Butylcarbamoyl-5-chloro-phenyl)-1-(2,5-difluoro-benzyl)-2-oxo-propyl]-carbamic acid tert-butyl ester Using general procedure 2 with [(R)-2-(2,5-Difluoro-phenyl)-1-(methoxy-methyl-carbamoyl)-ethyl]-carbamic acid tert-butyl ester (2.5 g, 7.4 mmol) and N-tert-Butyl-4-chloro-2-methyl-benzamide (5.0 g, 22 mmol) followed by purification by silica gel flash column chromatography gives the title compound.
¹HNMR
MS (m/e): 509 (M+1)
Step B

[(1R,2S)-3-(2-tert-Butylcarbamoyl-5-chloro-phenyl)-1-(2,5-difluoro-benzyl)-2-hydroxy-propyl]-carbamic acid tert-butyl ester Using general procedure 3 with [(R)-3-(2-tert-Butylcarbamoyl-5-chloro-phenyl)-1-(2,5-difluoro-benzyl)-2-oxo-propyl]-carbamic acid tert-butyl ester (2.5 g, 4.8 mmol) followed by purification by silica gel flash column chromatography gives the title compound.
¹HNMR
MS (m/e): 511 (M+1)
Step C 2-[(2S,3R)-3-Amino-4-(2,5-difluoro-phenyl)-2-hydroxy-butyl]-N-tert-butyl-4-chloro-benzamide Hydrochloride Using general deprotection procedure 1 with [(1R,2S)-3-(2-tert-butylcarbamoyl-5-chloro-phenyl)-1-(2,5-difluorobenzyl)-2-hydroxy-propyl]-carbamic acid tert-butyl ester (1.7 g, 3.3 mmol) gives the title compound.

¹HNMR (400 MHz, DMSO-d6) δ 8.15-8.12 (brd, J=3.2 Hz, 3H), 8.10 (s, 1H), 7.39 (s, 1H), 7.36-7.32 (m, 3H), 7.26-7.20 (m, 1H), 7.18-7.11 (m, 1H), 4.02 (dt, J=3.2, 8.8 Hz, 1H), 3.42-3.35 (m, 1H), 3.09 (dd, J=4.8, 14.8 Hz, 1H), 2.92-2.81 (m, 2H), 2,73 (dd, J=10.0, 14.0 Hz, 1H), 1.33 (s, 9H).

MS (m/e): 411 (M+1).

EXAMPLE 4

2-[(2S,3R)-3-Amino-4-(2-fluoro-phenyl)-2-methoxy-butyl]-N-tert-butyl-4-chloro-benzamide Hydrochloride

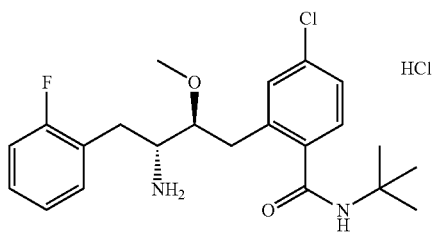

Step A

[(R)-3-(2-tert-Butylcarbamoyl-5-chloro-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (3.5 g, 11 mmol) and N-tert-Butyl-4-chloro-2-methyl-benzamide (7.3 g, 32 mmol) followed by purification using silica gel flash column chromatography gives the title compound.

¹HNMR

MS (m/e): 491 (M+1)

Step B

[(1R,2S)-3-(2-tert-Butylcarbamoyl-5-chloro-phenyl)-1-(2-fluoro-benzyl)-2-hydroxy-propyl]-carbamic acid tert-butyl ester Using general procedure 3 with [(R)-3-(2-tert-butylcarbamoyl-5-chloro-phenyl)-1-(2-fluoro-benzyl)-2-oxo-propyl]-carbamicacid tert-butyl ester (1.2 g, 2.4 mmol) followed by purification by silica gel flash column chromatography gives the title compound.

¹HNMR

MS (m/e): 493 (M+1)

Step C

[(1R,2S)-3-(2-tert-Butylcarbamoyl-5-chloro-phenyl)-1-(2-fluoro-benzyl)-2-methoxy-propyl]-carbamic acid tert-butyl ester To a solution of [(1R,2S)-3-(2-tert-Butylcarbamoyl-5-chloro-phenyl)-1-(2-fluoro-benzyl)-2-hydroxy-propyl]-carbamic acid tert-butyl ester (0.40 g, 0.81 mmol) in 5 mL of THF is added a 60% dispersion of sodium hydride in mineral oil (64 mg, 1.6 mmol) and the reaction is allowed to stir for 20 minutes at room temperature. Methyl iodide (0.05 mL, 0.81 mmol) is added and stirring is continued for an additional hour. The reaction is quenched by addition of water and the product is extracted into dichloromethane. The combined organic layers are dried over sodium sulfate, filtered, and concentrated under reduced pressure. Purification of the resultant crude residue by silica gel flash column chromatography gives the title compound.

¹HNMR

MS (m/e): 474 (M+1)

Step D

2-[(2S,3R)-3-Amino-4-(2-fluoro-phenyl)-2-methoxy-butyl]-N-tert-butyl-4-chloro-benzamide Hydrochloride Using general deprotection procedure 1 with [(1R,2S)-3-(2-tert-butylcarbamoyl-5-chloro-phenyl)-1-(2,5-difluoro-benzyl)-2-hydroxy-propyl]-carbamic acid tert-butyl ester (1.7 g, 3.3 mmol) followed by purification procedure 1 gives the title compound.

¹HNMR (400 , mHz, DMSO-d6) δ 8.02-7.975 (brs, 4H), 7.40 (dd,J=7.6, 8.0 Hz, 1H), 7.37-7.30 (m, 4), 7.22-7.15 (m, 2), 3.08 (dt,J=2.4, 6.8 Hz, 1H), 3.40-3.3 (m, 1h), 3.25 (s, 3H), 3.17 (dd,J=4 Hz, 1H), 3.08 (dd, 6.8,14.4 Hz, 1H), 2.9-2.76 (m, 2H), 1.34(s,9H).

MS (m/e): 407 (M+1).

EXAMPLE 5

2-[(2S,3R)-3-Amino-4-(2-fluoro-phenyl)-2-hydroxy-butyl]-N-tert-butyl-4-fluoro-benzamide Hydrochloride

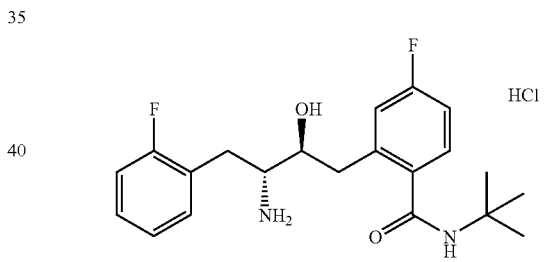

Step A

[(R)-3-(2-tert-Butylcarbamoyl-5-fluoro-phenyl)-1-(2-fluoro-benzyl)-2-oxo-propyl]-carbamic acid tert-butyl ester Using general procedure 2 with [(R)-2-(2-Fluoro-phenyl)-1-(methoxy-methyl-carbamoyl)-ethyl]-carbamic acid tert-butyl ester (1.6 g, 3.9 mmol) and N-tert-Butyl-4-fluoro-2-methyl-benzamide (3.0 g, 14 mmol) followed by purification by silica gel flash column chromatography gives the title compound.

¹HNMR

MS (m/e): 475 (M+1)

Step B

[(1R,2S)-3-(2-tert-Butylcarbamoyl-5-fluoro-phenyl)-1-(2-fluoro-benzyl)-2-hydroxy-propyl]-carbamic acid tert-butyl ester Using general procedure 3 with [(R)-3-(2-tert-Butylcarbamoyl-5-fluoro-phenyl)-1-(2-fluoro-benzyl)-2-oxo-propyl]-carbamic acid tert-butyl ester (1.8 g, 3.8 mmol) and purification by silica gel flash column chromatography gives the title compound.
¹HNMR
MS (m/e): 477 (M+1)

Step C

2-[(2S,3R)-3-Amino-4-(2-fluoro-phenyl)-2-hydroxy-butyl]-N-tert-butyl-4-fluoro-benzamide Hydrochloride Using general deprotection procedure 1 with [(1R,2S)-3-(2-tert-Butylcarbamoyl-5-fluoro-phenyl)-1-(2-fluoro-benzyl)-2-hydroxy-propyl]-carbamic acid tert-butyl ester (1.3 g, 2.7 mmol) gives the title compound.
¹HNMR (300 MHz, CD$_3$OD) δ 7.51-7.27 (m, 3H), 7.24-6.98 (m, 4H), 4.11-3.98 (m, 1H), 3.64-3.51 (m, 1H), 3.21 (m, 1H), 3.03-2.87 (m, 3H), 1.43 (s, 9H).
MS (m/e): 377 (M+1).

EXAMPLE 6

2-[(2S,3R)-3-Amino-4-(2-fluoro-phenyl)-2-hydroxy-butyl]-N-tert-butyl-4-methoxy-benzamide Hydrochloride

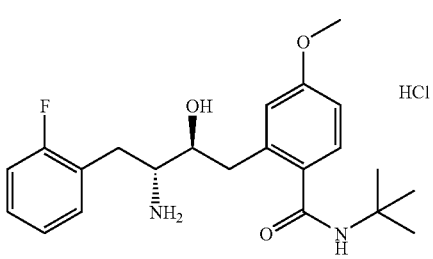

Step A

[(R)-3-(2-tert-Butylcarbamoyl-5-methoxy-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (1.4 g, 4.29 mmol) and N-tert-Butyl-4-methoxy-2-methyl-benzamide (2.8 g, 13 mmol) followed by purification by silica gel flash column chromatography gives the title compound.
¹HNMR
MS (m/e): 487 (M+1)

Step B

[(1R,2S)-3-(2-tert-Butylcarbamoyl-5-methoxy-phenyl)-1-(2-fluoro-benzyl)-2-hydroxy-propyl]-carbamic acid tert-butyl ester Using general procedure 3 with [(R)-3-(2-tert-butylcarbamoyl-5-methoxy-phenyl)-1-(2-fluoro-benzyl)-2-oxo-propyl]-carbamic acid tert-butyl ester (1.7 g, 3.5 mmol) and purification by silica gel flash column chromatography gives the title compound.
¹HNMR
MS (m/e): 489 (M+1)

Step C

2-[(2S,3R)-3-Amino-4-(2-fluoro-phenyl)-2-hydroxy-butyl]-N-tert-butyl-4-methoxy-benzamide Hydrochloride Using general deprotection procedure 1 with [(1R,2S)-3-(2-tert-butylcarbamoyl-5-methoxy-phenyl)-1-(2-fluoro-benzyl)-2-hydroxy-propyl]-carbamic acid tert-butyl ester (0.25 g, 0.5 mmol) gives the title compound.
¹HNMR (300 MHz, CD$_3$OD) δ 7.40-7.34 (m, 3H), 7.21-7.15 (m, 2H), 6.87 (dt, J=9.5, 2.4 Hz, 2H), 4.05-4.02 (m, 1H), 3.81 (s, 3H), 3.70-3.58 (m, 1H), 3.24 (dd, J=14.6, 5.1 Hz, 1H), 3.03-2.87 (m, 2H), 1.45 (s, 9H).
MS (m/e): 389 (M+1).

EXAMPLE 7

2-[(2S,3R)-3-Amino-4-(2-fluoro-phenyl)-2-hydroxy-butyl]-N-tert-butyl-5-chloro-benzamide Hydrochloride

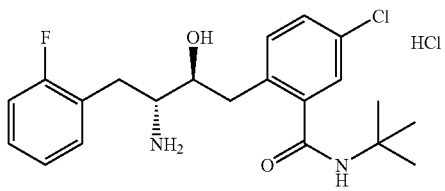

Step A

[(R)-3-(2-tert-Butylcarbamoyl-4-chloro-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (1.56 g, 4.8 mmol) and N-tert-butyl-5-chloro-2-methyl-benzamide (3.25 g, 14 mmol), followed by purification by silica gel flash column chromatography gives the title compound.
¹HNMR
MS (m/e): 491 (M+1)

Step B

[(1R,2S)-3-(2-tert-Butylcarbamoyl-4-chloro-phenyl)-1-(2-fluoro-benzyl)-2-hydroxy-propyl]-carbamic acid tert-butyl ester Using general procedure 3 with [(R)-3-(2-tert-butylcarbamoyl-4-chloro-phenyl)-1-(2-fluoro-benzyl)-2-oxo-propyl]-carbamic acid tert-butyl ester (0.30 g, 0.7 mmol) and purification by silica gel flash column chromatography gives the title compound.
¹HNMR
MS (m/e): 493 (M+1)

Step C

2-[(2S,3R)-3-Amino-4-(2-fluoro-phenyl)-2-hydroxy-butyl]-N-tert-butyl-5-chloro-benzamide Hydrochloride Using general deprotection procedure 1 with [(1R,2S)-3-(2-tert-butylcarbamoyl-4-chloro-phenyl)-1-(2-fluoro-benzyl)-2-hydroxy-propyl]-carbamic acid tert-butyl ester (0.45 g, 0.9 mmol) gives the title compound.

¹HNMR (300 MHz, CD₃OD) δ 8.08 (s, 1H), 7.32-7.26 (m, 5H), 7.13-7.06 (m, 2H), 3.97 (s, 1H), 3.49 (s, 1H), 3.16 (dd, J=14.5, 4.1 Hz, 1H), 2.89 (d, J=9.4 Hz, 1H), 2.84 (d, J=6.4 Hz, 2H), 1.37 (s, 9H).

MS (m/e): 393 (M+1).

EXAMPLE 8

2-[(2S,3R)-3-Amino-4-(2-fluoro-phenyl)-2-hydroxy-butyl]-N-tert-butyl-6-methyl-benzamide Hydrochloride

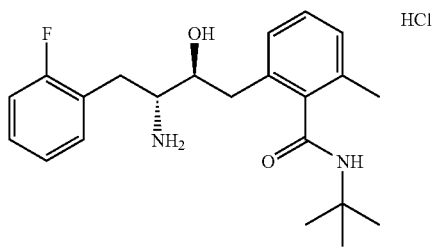

Step A

[(R)-3-(2-tert-Butylcarbamoyl-3-methyl-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (2.65 g, 8.1 mmol) and N-tert-butyl-2,6-dimethyl-benzamide (5.0 g, 24 mmol), followed by purification by silica gel flash column chromatography gives the title compound.

¹HNMR

MS (m/e): 471 (M+1)

Step B

[(1R,2S)-3-(2-tert-Butylcarbamoyl-3-methyl-phenyl)-1-(2-fluoro-benzyl)-2-hydroxy-propyl]-carbamic acid tert-butyl ester Using general procedure 3 with [(R)-3-(2-tert-butylcarbamoyl-3-methyl-phenyl)-1-(2-fluoro-benzyl)-2-oxo-propyl]-carbamic acid tert-butyl ester (1.8 g, 3.8 mmol) and purification by silica gel flash column chromatography gives the title compound.

¹HNMR

MS (m/e): 473 (M+1)

Step C

2-[(2S,3R)-3-Amino-4(2-fluoro-phenyl)-2-hydroxy-butyl]-N-tert-butyl-6-methyl-benzamide Hydrochloride Using general deprotection procedure 1 with [(1R,2S)-3-(2-tert-butylcarbamoyl-3-methyl-phenyl)-1-(2-fluoro-benzyl)-2-hydroxy-propyl]-carbamic acid tert-butyl ester (0.90 g, 1.9 mmol) gives the title compound.

¹HNMR (300 MHz, CD₃OD) δ 7.36 (t, J=7.6 Hz, 2H), 7.24-7.14 (m, 5H), 4.04-3.99 (m, 1H), 3.58-3.54 (m, 1H), 3.25 (d, J=5.2 Hz, 1H), 3.19 (s, 1H), 2.97-2.89 (m, 1H), 2.35 (s, 3H), 1.46 (s, 9H).

MS (m/e): 393 (M+1).

EXAMPLE 9

2-[(2S,3R)-3-Amino-4-(2-fluoro-phenyl)-2-hydroxy-butyl]-N-tert-butyl-5-methyl-benzamide Hydrochloride

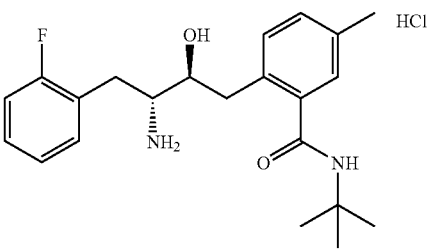

Step A

[(R)-3-(2-tert-Butylcarbamoyl-4-methyl-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (2.15 g, 6.6 mmol) and N-tert-butyl-2,5-dimethyl-benzamide (4.0 g, 20 mmol), followed by purification by silica gel flash column chromatography gives the title compound.

¹HNMR

MS (m/e): 471 (M+1)

Step B

[(1R,2S)-3-(2-tert-Butylcarbamoyl-4-methyl-phenyl)-1-(2-fluoro-benzyl)-2-hydroxy-propyl]-carbamic acid tert-butyl ester Using general procedure 3 with [(R)-3-(2-tert-Butylcarbamoyl-4-methyl-phenyl)-1-(2-fluoro-benzyl)-2-oxo-propyl]-carbamic acid tert-butyl ester (1.4 g, 2.9 mmol) and purification by silica gel flash column chromatography gives the title compound.

¹HNMR

MS (i/e): 473 (M+1)

Step C

2-[(2S,3R)-3-Amino-4-(2-fluoro-phenyl)-2-hydroxy-butyl]-N-tert-butyl-5-methyl-benzamide Hydrochloride Using general deprotection procedure 1 with [(1R,2S)-3-(2-tert-butylcarbamoyl-4-methyl-phenyl)-1-(2-fluoro-benzyl)-2-hydroxy-propyl]-carbamic acid tert-butyl ester (1.1 g, 2.3 mmol) gives the title compound.

¹HNMR (300 MHz, CD₃OD) δ 7.39-7.34 (m, 2H), 7.25-7.12 (m, 5H), 4.12-4.07 (m, 1H), 3.50 (dt, J=9.0, 3.9 Hz, 1H), 3.23 (dd, J=14.6, 3.9 Hz, 1H), 2.96 (d, J=10.1 Hz, 1H), 2.88 (dd, J=11.3, 8.1 Hz, 1H), 2.36 (s, 3H), 1.46 (s, 9H).

MS (m/e): 373 (M+1).

EXAMPLE 10

2-[(2S,3R)-3-Amino-4-(2-fluoro-phenyl)-2-hydroxy-butyl]-N-tert-butyl-6-chloro-benzamide Hydrochloride

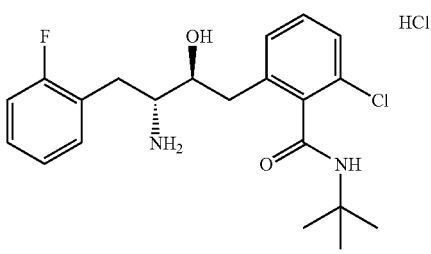

Step A

[(R)-3-(2-tert-Butylcarbamoyl-3-chloro-phenyl)-1-(2-fluoro-benzyl)-2-oxo-propyl]-carbamic acid tert-butyl ester Using general procedure 2 with [(R)-2-(2-fluoro-phenyl)-1-(methoxy-methyl-carbamoyl)-ethyl]-carbamic acid tert-butyl ester (1.5 g, 4.6 mmol) and N-tert-butyl-2-chloro-6-methyl-benzamide (1.5 g, 4.6 mmol), followed by purification by silica gel flash column chromatography gives the title compound.
$^1$HNMR
MS (m/e): 491 (M+1)

Step B

[(1R,2S)-3-(2-tert-Butylcarbamoyl-3-chloro-phenyl)-1-(2-fluoro-benzyl)-2-hydroxy-propyl]-carbamic acid tert-butyl ester Using general procedure 3 with [(R)-3-(2-tert-Butylcarbamoyl-3-chloro-phenyl)-1-(2-fluoro-benzyl)-2-oxo-propyl]-carbamic acid tert-butyl ester (1.6 g, 3.3 mmol) and purification by silica gel flash column chromatography gives the title compound.
$^1$HNMR
MS (m/e): 493 (M+1)

Step C

2-[(2S,3R)-3-Amino-4-(2-fluoro-phenyl)-2-hydroxy-butyl]-N-tert-butyl-6-chloro-benzamide Hydrochloride Using general deprotection procedure 1 with [(1R,2S)-3-(2-tert-Butylcarbamoyl-3-chloro-phenyl)-1-(2-fluoro-benzyl)-2-hydroxy-propyl]-carbamic acid tert-butyl ester (980 mg, 2.0 mmol) gives the title compound.
$^1$HNMR (300 MHz, CDCl$_3$) δ 8.16 (s, 2H), 7.36 (t, J=7.3 Hz, 1H), 7.26-7.16 (m, 4H), 7.07-6.97 (m, 2H), 6.05 (s, 1H), 4.29 (s, 1H), 3.55 (s, 1H), 3.16 (dd, J=14.3, 4.3 Hz, 1H), 2.98 (dd, J=29.3, 9.4 Hz, 1H), 2.83 (d, J=6.0 Hz, 2H), 1.45 (s, 9H).
MS (m/e): 393 (M+1).

The compound of formula I is preferably formulated in a unit dosage form prior to administration. Therefore, yet another aspect of the present invention is a pharmaceutical composition comprising a compound of formula I and one or more pharmaceutically acceptable carriers, diluents or excipients.

The present pharmaceutical compositions are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

The pharmacological profile of the present compounds may be demonstrated as follows:

Human Recombinant DPIV Activity Assay

The DPIV assay uses a fluorometric end point assay (excitation 355 nm; emission 460 nm), enriched human recombinant DPIV enzyme (21.3 µU/µl), and Gly-Pro-AMC (Bachem I-1225) as substrate (0.02 mM). Secreted DPIV (lacking membrane anchor) is enriched from HEK293 cell culture supernatant by ultrafiltration, ultra-centrifugation, and size-exclusion chromatography. IC50 values of the compounds are calculated based on a 12 points concentration response curve. Each concentration is measured in duplicate. The assay is validated by plate variability and conformity, inter-plate variability, signal window, and minimum significant ration of IC50. A MSR is calculated based on a test/retest analysis and a retrospective analysis. The MSR value is 1.8.

Using this assay the preferred compounds of the invention described within the examples show activity with an IC50 less than or equal to 100 µM.

| Example | IC50 (µM) |
|---------|-----------|
| 6 | 0.098 |
| 7 | 0.134 |

We claim:

1. A compound of the formula I:

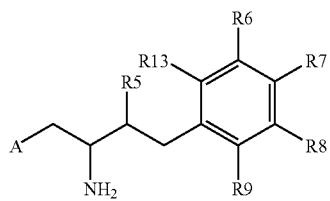

(I)

or a pharmaceutically acceptable salt thereof, wherein
A is

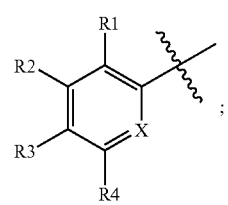

R1 is halo;
R2, R3, and R4 are independently selected from H and halo;
X is CH;
R5 is —OR12;

R6 is selected from H, halo, $C_1$-$C_6$ alkyl, and $C_1$-$C_6$ alkoxy;
R7 and R8 are independently selected from H, halo, and $C_1$-$C_6$ alkyl;
R9 is —C(O)NR10R11;
R10 and R11 are independently selected from H and $C_1$-$C_6$ alkyl;
R12 is selected from H and $C_1$-$C_6$ alkyl; and R13 is H.

2. A compound according to claim 1 of the formula IIb:

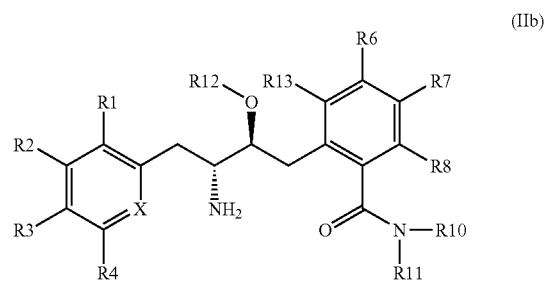

(IIb)

or a pharmaceutically acceptable salt thereof.

3. A compound according to claim 1 wherein R1 is F, and R2 and R3 are independently selected from H and F.

4. A compound according to claim 3 wherein R1 and R4 are F.

5. A compound according to claim 4 wherein R1 is F and R4 is either H or F.

6. A compound according to claim 1 wherein R3 is selected from H and F.

7. A compound according to claim 6 wherein R3 is F.

8. A compound according to claim 1 wherein R2 is H.

9. A compound according to claim 1 wherein R6, R7, and R8 are independently selected from H, F, Cl, and $CH_3$.

10. A compound according to claim 9 wherein R6 is Cl, R7, and R8 are H.

11. A compound according to claim 1 wherein R10 is H.

12. A compound according to claim 1 wherein R11 is t-butyl.

13. A compound according to claim 1 wherein R12 is H.

14. A pharmaceutical composition comprising a compound of formula I according to claim 1:

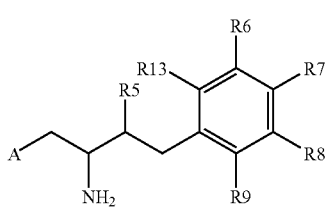

(I)

or a pharmaceutically acceptable salt thereof, and
a pharmaceutically acceptable diluent or carrier.

15. A pharmaceutical composition of claim 14 additionally comprising metformin.

16. A method for therapeutic treatment of a condition selected from type II diabetes, obesity, hyperglycemia and a lipid disorder, which comprises administering an effective amount of a compound of formula I according to claim 1:

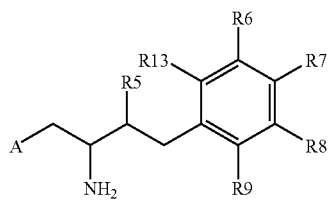
(I)

or a pharmaceutically acceptable salt thereof to a human being or animal in need thereof.

17. A method according to claim 16 wherein said lipid disorder is selected from dyslipidemia, hyperlipidemia, hypertriglyceridemia, hypercholesterolemia, low HDL and high LDL.

* * * * *